US008379978B2

(12) United States Patent
Eguchi et al.

(10) Patent No.: US 8,379,978 B2
(45) Date of Patent: Feb. 19, 2013

(54) CONTACT AREA MEASUREMENT DEVICE AND METHOD FOR MEASURING CONTACT AREA

(75) Inventors: Masao Eguchi, Fuchu (JP); Takashi Shibamiya, Fuchu (JP); Manabu Sawayanagi, Fukuroi (JP); Tomoyuki Miyazaki, Fukuroi (JP)

(73) Assignees: Tokyo University of Agriculture and Technology, Fuchu-shi (JP); NSK-Warner K. K., Shinagawa-ku (JP)

( * ) Notice: Subject to any disclaimer, the term of this patent is extended or adjusted under 35 U.S.C. 154(b) by 307 days.

(21) Appl. No.: 12/736,163

(22) PCT Filed: Feb. 23, 2009

(86) PCT No.: PCT/JP2009/053222
§ 371 (c)(1),
(2), (4) Date: Sep. 16, 2010

(87) PCT Pub. No.: WO2009/116359
PCT Pub. Date: Sep. 24, 2009

(65) Prior Publication Data
US 2011/0013835 A1 Jan. 20, 2011

(30) Foreign Application Priority Data

Mar. 17, 2008 (JP) .................................. 2008-067584
Aug. 1, 2008 (JP) .................................. 2008-199469

(51) Int. Cl.
*G06K 9/00* (2006.01)
(52) U.S. Cl. ........................................ 382/168; 382/171
(58) Field of Classification Search .................. None
See application file for complete search history.

(56) References Cited

U.S. PATENT DOCUMENTS

2004/0090634 A1* 5/2004 Mathur et al. ................. 356/497
2008/0027582 A1* 1/2008 Obinata et al. ................ 700/260

FOREIGN PATENT DOCUMENTS

JP H11-351984 12/1999
JP 2000-254884 9/2000

(Continued)

OTHER PUBLICATIONS

Masao Eguchi, Takashi Yamamoto, "Shear characteristics of a boundary film for a paper-based wet friction material: friction and real contact area measurement", Tribology International, vol. 38, Issue 3, Mar. 2005, pp. 327-335.*

(Continued)

*Primary Examiner* — Li Liu
(74) *Attorney, Agent, or Firm* — Masuvalley & Partners

(57) ABSTRACT

A novel contact area measuring apparatus is provided. The contact area measuring apparatus includes a light transmissive substrate 6 in contact with a specimen 7, illumination means for illuminating the light transmissive substrate 6 with white light from the opposite side of the light transmissive substrate 6 to the specimen 7, interference image acquisition means 11 for acquiring an interference image produced by the light reflected off the specimen 7 and the light reflected off the light transmissive substrate 6, intensity histogram creation means for creating an intensity histogram from information on the intensity of the interference image, and contact area computation means for calculating a contact area from the intensity histogram. The interference image acquisition means 11 acquires an interference image and information on the intensity of the interference image. The intensity histogram creation means forms separate RGB intensity information from the information on the intensity of the interference image and creates a G-intensity histogram. The contact area computation means separates the intensity histogram into a plurality of normal distributions by using optimized approximation of complex normal distribution and calculates the contact area from the lowest-intensity normal distribution.

20 Claims, 37 Drawing Sheets

FOREIGN PATENT DOCUMENTS

| | | |
|---|---|---|
| JP | 2005-0055413 | 3/2005 |
| JP | 2005-257343 | 9/2005 |
| WO | WO2006/030570 | 3/2006 |

OTHER PUBLICATIONS

"Measurement of real contact area using intensity of white light interferometry" Takashi Shibamiya, Masao Eguchi, Takashi Yamamoto Japanese Society of Tribologists, Proceedings of Tribology Conference, May 2008, Tokyo, p. 11,12.

"Partial Slip Visualization at Contact Surface with the Correlation Method" Jun Liu, Kahtaro Ohba, Koji Kato, Hikaru Inooka Journal of the Visualization Society of Japan, 15, 57 (1997), p. 133-139.

"A study on the Rolling-Sliding Friction of Rubber and the Slip in Contact Area" Tomoaki Iwai, Kouki Hasegawa, Seiichi Ueda, Yoshitake Uchiyama Tribologists, 50, 8 (2005), p. 620-627.

"Sensing Slip and Its Direction Using Quartz Resonators" Shigenobu Muraoka Transactions of Society of Instrument and Control Engineers, 36, 8 (2000), p. 639-344.

"Analysis of real area of contact under non-lubricated reciprocating motion using white light interference intensity" Takashi Shibamiya, Masao Eguchi, Takashi Yamamoto Japanese Society of Tribologists, Proceeding s of Tribology Conference, Apr. 26, 2007 vol. 2007-5, p. 89-90.

"Measurement of Real Contact Area Using White Light Interferometry for Low-Reflecting Rough Surface under Non-Lubricated Conditions" Masao Eguchi, Takashi Yamamoto Tribologist, VII.50, No. 6, (2005) p. 471-478.

"An analysis of Stick/Slip Region of Real Contact at the Starting of Motion Using White Light Interference Intensity" Masao Eguchi, Takashi Shibamiya, Takashi Yamamoto Japanese Society of Tribologists, Proceedings of Tribology Conference, Sep. 1, 2008, vol. 2008-9, p. 443-444.

"Micro-Slip against Rubber in Friction Drives" Koji Kato Tribologist, vol. 42, No. 5, (1997) p. 369-374.

"Waveform Data Processing for Scientific Measurement" Shigeo Minami(editor) CQ Publishing Co., Ltd. (1986), p. 90-93.

"Friction/Wear tests and their applications" Japanese Society of Tribologists, Yokendo Co., Ltd. (2007), p. 120-121.

"Tribology Handbook" Japanese Society of Tribologists, Yokendo Co., Ltd. (2001) p. 13-15.

"Measurement of the Area and Visualization of the Stick/Slip Region of Real Contact Using White Light Interferometry" Masao Eguchi, Takashi Shibamiya, Takashi Yamamoto No. 4, Aug. 2, 2008 p. 153-154.

"Compliance of Elastic Bodies in Contact," Mindlin, R.D, J. Applied Mechanics, 16, (1949) p. 259-268.

* cited by examiner

CONTACT AREA MEASUREMENT DEVICE AND METHOD FOR MEASURING CONTACT AREA

This application is a National Stage application under 35 U.S.C. §371 of International Application Serial No. PCT/JP2009/053222, filed on Feb. 23, 2009, and claims the priority benefit under 35 U.S.C. §119 of Japanese Patent Application No. 2008-067584, filed Mar. 17, 2008, and Japanese Patent application Serial No. 2008-199469, filed Aug. 1, 2008, which are hereby expressly incorporated by reference in their entirety for all purposes.

TECHNICAL FIELD

The present invention relates to a novel contact area measuring apparatus and method. More specifically, it relates to a novel apparatus and method for visualizing a contact area between two surfaces in contact with each other and statistically extracting a real contact area from the visualized image based only on an intensity histogram of the image without requiring a threshold for binarization. The invention also relates to a novel apparatus and method for measuring and visualizing the distribution of a stick region and a slip region in a real contact area by using an intensity histogram.

BACKGROUND OF THE INVENTION

Conventionally, a contrast method or a total reflection method is used to acquire an image that visualizes a contact area. The acquired image is then binarized using an intensity threshold value to extract the real contact area. When a contrast method is used to visualize the real contact area, materials to be visualized are limited and the accuracy in extracting a true contact region is poor. On the other hand, in the total reflection method, since a prism is used to observe a contact area obliquely, the aspect ratio of an image is not one and the contact area cannot be brought into focus very well. In the conventional extracting method, the image acquired by using either of the methods described above undergoes (1) binarization by visually comparing the acquired image with the original image to extract an image. In this case, the threshold setting and hence the extraction result differ person to person, and it takes a long time to carry out the whole procedure. (2) In the image analysis field, an Otsu method is frequently used to determine the threshold, but the method is originally directed to typical images and used to extract an object from the background. The principle according to which the Otsu method extracts an object uses the fact that the threshold is present in the valley between adjacent peaks in an intensity histogram. There is no obvious reason for directly applying the method to the problems described above, and the method is not applicable or accurate.

FIG. 14 shows the relationship between an intensity histogram and its relative threshold for binarization. Each of the left raised portions represents a histogram for a real contact area and the vicinity thereof. In a conventional method, since the region having intensity smaller than or equal to a threshold is extracted as a real contact area, it is difficult to rationally determine the threshold.

On the other hand, a white polarized light interferometry system is proposed in Japanese Patent No. 3,718,837 to acquire a contact area image viewed from the front. In this system, the real contact area can be accurately visualized, theoretically and experimentally, based on the relationship between a clearance and intensity using the acquired image along with an RGB-AND method. The RGB-AND method does not require an exact threshold, which allows for a real contact area to be extracted. That is, the intensity values of an interference image formed using the three RGB colors are simultaneously evaluated, and regions in which a real contact area has an achromatic color, the RGB intensity values have the same value, are extracted by using rough thresholds. A real contact area is eventually determined by performing logical product (AND) operation on the extracted regions. That is, when two-beam interferometry is used, since a real contact area (0-th interference fringe) has an achromatic color, the RGB intensity values have the same value, as shown in FIG. 15. Using this fact, one can perform logical product (AND) operation on the three RGB images binarized by the rough thresholds to extract a real area of contact.

On the other hand, when a tangential force is applied to a real contact area between two frictional surfaces that are made of plastic materials and in contact with each other, the real contact area grows. When the two surfaces are made of elastic materials, it is believed that the ratio of a "slip region" to a "stick region" (see FIG. 16) changes, and that the entire real contact area eventually becomes the "slip region" and undergoes macroscopic slippage (see Non-patent Document 1: Takashi Shibamiya, Masao Eguchi, and Takashi Yamamoto, "Measurement of real area of contact using intensity of white light interferometry," Japanese Society of Tribologists, Proceedings of Tribology Conference, (May, 2008, Tokyo), page 11-12).

Further, a correlation method to identify and visualize stick and slip regions between contact surfaces in a slipping contact state are proposed (see Non-patent Document 2: Liu Jun, Kohtaro Ohba, Koji Kato, and Hikaru Inooka, "Partial slip visualization at contact surface with the correlation method", Journal of the Visualization Society of Japan, 15, 57 (1995), pp. 133-139). Also, particle tracking velocimetry (PTV) are used to identify and visualize stick and slip regions between contact surfaces in a rolling-slipping contact state (see Non-patent Document 3: Tomoaki Iwai, Kouki Hasegawa, Seiichi Ueda, and Yoshitaka Uchiyama, "A Study on the Rolling-Sliding Friction of Rubber and the Slip in Contact Area," Tribologists, 50, 8 (2005), pp. 620-627).

In the methods described above, which use particle image velocimetry (PIV) in a broad sense, one of the objects has a tracer (tracking marker) and the contact surfaces between them is visualized in a certain method (for example, using the fact that a real contact surface has different contrast). By successively forming only the visualized images, the shift in the marker position between two images are detected so that the stick and slip contact states can be analyzed and visualized.

Alternatively, the detection of "slippage" is carried out by preparing an acceleration sensor or a quartz oscillator and measuring the change in the signal therefrom. (see Non-patent Document 4: Shigenobu Muraoka, "Sensing Slip and Its Direction Using Quartz Resonators," Transactions of the Society of Instrument and Control Engineers, 36, 8 (2000), pp. 639-644)

However, the above-described methods are problematic in that intensity values of the RGB three elements and the thresholds therefor, even though the thresholds can be rough values, are required and that the result tends to change depending on how well the thresholds can be set. Further, such exact/approximate thresholds are affected by illumination at the time of measurement, the material of an object under test, and characteristics of a camera used in the measurement and the presence of the thresholds disadvantageously requires calibration for each combination thereof.

Further, there are also the following other disadvantages: (1) since a contrast method is used to visualize a contact surface in conventional observation methods, the material of an object under test is limited and the accuracy in extracting a real contact region is poor, (2) it is necessary to attach a tracking marker onto a surface to be observed, (3) it is also necessary in PIV-based analysis to set an observation window whose side ranges from several pixels to several tens of pixels, and (4) a large amount of computation in PIV requires a high-speed computer.

Alternatively, to detect "slippage" by preparing an acceleration sensor or a quartz oscillator and measuring the change in the signal therefrom, a space for placing the sensor or the oscillator, variation in sensitivity depending on the location of the sensor or the oscillator, and other variety of problems need to be solved.

The present invention is proposed in view of the above aforementioned problems.

The present invention provides a novel contact area measuring apparatus and method for visualizing the contact area between two surfaces in contact with each other and extracting the real contact area from the visualized image without requiring a threshold for binarization. Further, the present invention provides a novel apparatus and method for measuring and visualizing the distribution of a stick region and a slip region in a real contact area using an intensity histogram.

SUMMARY

In accordance with one aspect of the present invention, a contact area measuring apparatus is provided that includes a light transmissive substrate in contact with a specimen, illumination means for illuminating the light transmissive substrate with white light from the opposite side of the light transmissive substrate to the specimen, interference image acquisition means for acquiring an interference image produced by the light reflected off the specimen and the light reflected off the light transmissive substrate, intensity histogram creation means for creating an intensity histogram from information on the intensity of the interference image, and contact area computation means for calculating a contact area from the intensity histogram.

The interference image acquisition means preferably, but not limited to, acquires an interference image and information on the intensity of the interference image. The intensity histogram creation means preferably, but not limited to, forms separate RGB intensity information from the information on the intensity of the interference image and creates a G-intensity histogram. The contact area computation means preferably, but not limited to, calculates the contact area by performing optimized approximation of complex normal distribution on the intensity histogram. The contact area computation means preferably, but not limited to, separates the intensity histogram into a plurality of normal distributions by using optimized approximation of complex normal distribution and calculates the contact area from the lowest-intensity normal distribution.

In accordance with a second aspect of the present invention, there is provided a method for measuring and extracting a real contact area. The method includes the steps of placing a specimen on a light transmissive substrate so that the specimen comes into contact with the light transmissive substrate, illuminating the light transmissive substrate with white light from the opposite side of the light transmissive substrate to the specimen, acquiring an interference image produced by the light reflected off the specimen and the light reflected off the light transmissive substrate, creating an intensity histogram from information on the intensity of the interference image, and calculating a contact area from the intensity histogram.

In the interference image acquisition step, an interference image and information on the intensity of the interference image are preferably, but not necessarily, acquired. In the intensity histogram creation step, separate RGB intensity information is preferably, but not necessarily, formed from the information on the intensity of the interference image and a G-intensity histogram is preferably, but not necessarily, created. In the contact area computation step, the contact area is preferably, but not necessarily, calculated by performing optimized approximation of complex normal distribution on the intensity histogram. In the contact area computation step, the intensity histogram is preferably, but not necessarily, separated into a plurality of normal distributions by using optimized approximation of complex normal distribution and the contact area is preferably, but not necessarily, calculated from the lowest-intensity normal distribution.

In accordance with a third aspect of the present invention, a contact area measuring apparatus is provide that includes a light transmissive substrate in contact with a specimen, driving means for moving the specimen and the light transmissive substrate relative to each other, illumination means for illuminating the light transmissive substrate with white light from the opposite side of light transmissive substrate to the specimen, interference image acquisition means for acquiring an interference image produced by the light reflected off the specimen and the light reflected off the light transmissive substrate, intensity histogram creation means for creating an intensity histogram from information on the intensity of the interference image, and image analysis and computation means for calculating an intensity difference histogram from the intensity histogram.

The intensity histogram creation means preferably, but not limited to, forms separate RGB intensity information from the information on the intensity of the interference image and creates a G-intensity histogram. The image analysis and computation means preferably, but not limited to, calculates an intensity difference histogram from the intensity histogram and determines the region of the intensity difference histogram that has positive values.

In accordance with a fourth aspect of the present invention, a contact area measuring apparatus is provided that includes a light transmissive substrate in contact with a specimen, driving means for moving the specimen and the light transmissive substrate relative to each other, illumination means for illuminating the light transmissive substrate with white light from the opposite side of the light transmissive substrate to the specimen, interference image acquisition means for acquiring an interference image produced by the light reflected off the specimen and the light reflected off the light transmissive substrate, and image analysis and computation means for using information on the intensity of the interference image as a tracking marker.

The interference image acquisition means preferably, but not limited to, acquires an interference image and information on the intensity of the interference image. The image analysis and computation means preferably, but not limited to, calculates a velocity vector by using the information on the intensity of the interference image as a tracking marker.

In accordance with a fifth aspect of the present invention, there is provide a method for measuring and extracting a real contact area. The method includes the steps of placing a specimen on a light transmissive substrate so that the specimen comes into contact with the light transmissive substrate, moving the specimen and the light transmissive substrate relative to each other, illuminating the light transmissive substrate with white light from the opposite side of the light transmissive substrate to the specimen, acquiring an interference image produced by the light reflected off the specimen and the light reflected off the light transmissive substrate, creating an intensity histogram from information on the intensity of the interference image, and calculating an intensity difference histogram from the intensity histogram.

In the intensity histogram creation step, separate RGB intensity information is preferably, but not necessarily, formed from the information on the intensity of the interference image and a G-intensity histogram is preferably, but not necessarily, created. An intensity difference histogram is preferably, but not necessarily, calculated from the intensity histogram, and the region of the intensity difference histogram that has positive values is preferably, but not necessarily, determined.

In accordance with a sixth aspect of the present invention, there is provided a method for measuring and extracting a real contact area. The method includes the steps of placing a specimen on a light transmissive substrate so that the specimen comes into contact with the light transmissive substrate, moving the specimen and the light transmissive substrate relative to each other, illuminating the light transmissive substrate with white light from the opposite side of the light transmissive substrate to the specimen, acquiring an interference image produced by the light reflected off the specimen and the light reflected off the light transmissive substrate, and using information on the intensity of the interference image as a tracking marker.

In the interference image acquisition step, an interference image and information on the intensity of the interference image are preferably, but not necessarily, acquired. A velocity vector is preferably, but not necessarily, calculated by using the information on the intensity of the interference image as a tracking marker.

DETAILED DESCRIPTION

Figure 1:
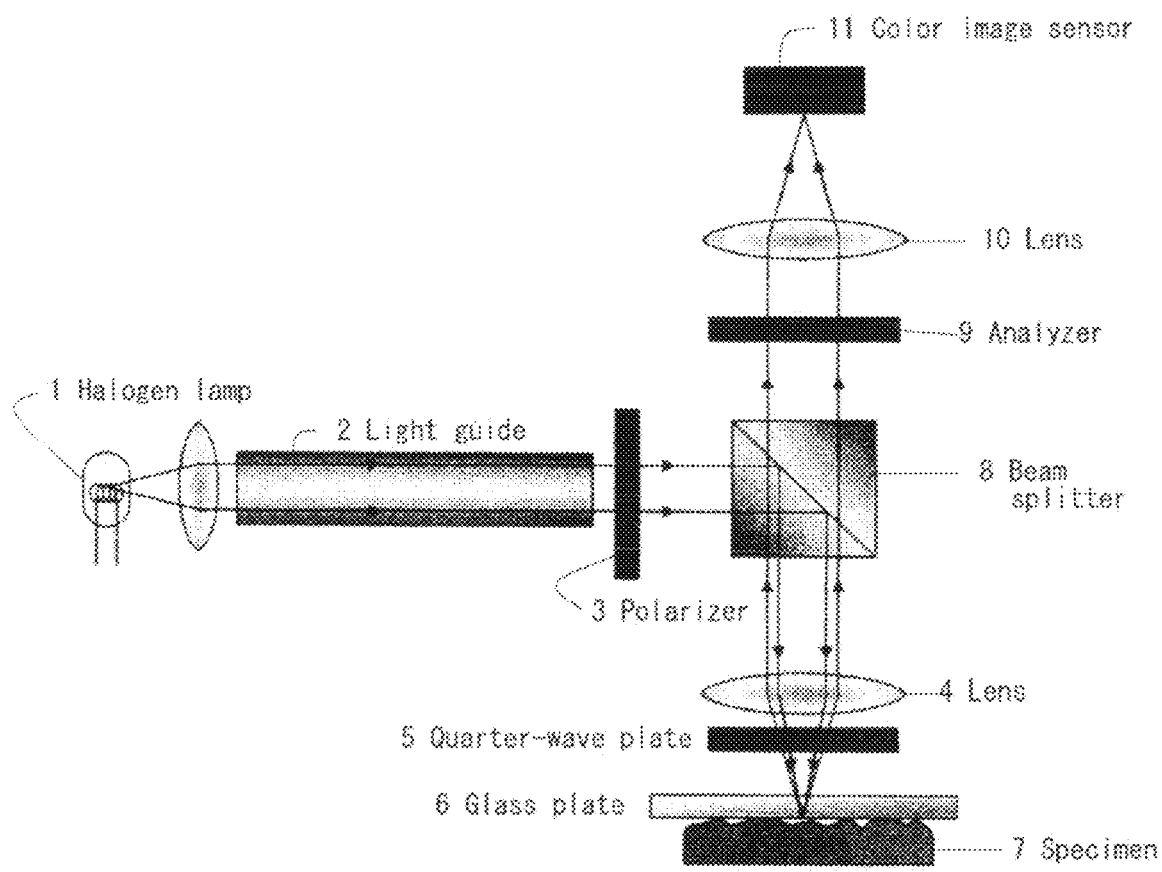
FIG. 1 shows a measuring system using white light interferometry.

Embodiments of the present invention will be described hereinafter with reference to the accompanying drawings, in which preferred exemplary embodiments of the invention are shown. The ensuing description is not intended to limit the scope, applicability or configuration of the disclosure. Rather, the ensuing description of the preferred exemplary embodiments will provide those skilled in the art with an enabling description for implementing preferred exemplary embodiments of the disclosure. It should be noted that this invention may be embodied in different forms without departing from the spirit and scope of the invention as set forth in the appended claims.

Embodiments of the present invention are directed to a contact area measuring apparatus and method for visualizing a contact area between two frictional surfaces and statistically extracting the real contact area based on the intensity histogram of the visualized image without requiring a threshold for binarization. Further, embodiments of the present invention are directed to a contact area measuring apparatus and method for measuring and visualizing the distribution of a stick region and a slip region in the real contact area using the intensity histogram.

According to one embodiment, the contact area measuring apparatus includes a light transmissive substrate in contact with a specimen, illumination means for illuminating the light transmissive substrate with white light from the opposite side of the light transmissive substrate to the specimen, interference image acquisition means for acquiring an interference image produced by the light reflected off the specimen and the light reflected off the light transmissive substrate, intensity histogram creation means for creating an intensity histogram from information on the intensity of the interference image, and contact area computation means for calculating a contact area from the intensity histogram.

A process for measuring the contact area according to the present invention includes the steps of: (1) placing a specimen on a light transmissive substrate so that they come into contact with each other; (2) illuminating the light transmissive substrate with white light from the opposite side of the light transmissive substrate to the specimen; (3) acquiring an interference image produced by the light reflected off the specimen and the light reflected off the light transmissive substrate; (4) creating an intensity histogram from information on the intensity of the interference image; and, (5) calculating a contact area from the intensity histogram.

The interference image acquisition means of the contact area measuring apparatus acquires an interference image and information on the intensity of the interference image. White polarized light interferometry, which does not depend on the material of the specimen or the surface characteristics thereof, and a camera having a wide dynamic range are used to acquire an image that visualizes a contact area. Specifically, a stereo microscope and white polarized light interferometry are used to visualize a minute clearance produced at the interface between the light transmissive substrate and the specimen pressed thereagainst, and a digital camera is used to acquire an interference fringe image produced at the periphery of the contact area. Low coherency of the white light and resultant low intensity of higher-order dark interference fringes, which are not related to a real contact area, allow only the real contact area to be readily extracted. The light transmissive substrate can, for example, be made of glass, sapphire, or polycarbonate.

The intensity histogram creation means of the contact area measuring apparatus forms separate RGB intensity information from the information on the intensity of the interference image and creates a G-intensity histogram. When a color digital camera is used, separate RGB intensity information is formed by using image processing software to process an acquired image, and then an intensity histogram is created only from the information on the intensity of the G-image. The reason for this is that the G element has the highest sensitivity. It should be noted that the object of the invention can be achieved by using an R-intensity histogram or a B-intensity histogram as well as the G-intensity histogram.

The contact area computation means of the contact area measuring apparatus separates the intensity histogram into a plurality of normal distributions by using optimized approximation of complex normal distribution and calculates the contact area from the lowest-intensity normal distribution. A G-intensity histogram of an interference image of a real contact area in typical rough but nominal flat surface contact has a complex normal distribution in which two or more normal distributions overlap with each other. The distribution is separated into a plurality of normal distributions by using software-based nonlinear optimization. Among them, a normal distribution that fits most with the lowest-intensity normal distribution is selected. The region (the number of pixels) surrounded by the selected normal distribution corresponds to the real contact area.

The contact area measuring apparatus and the process for measuring the contact area, according to the present invention, are applicable to technical fields requiring data on prototype/technology developments directly related to: development and performance evaluation of frictional materials used for brakes, clutches, and other components; and improvement in contact/friction maintenance between surfaces and tires, shoe soles, and other products. Other fields to which the contact area measuring apparatus and the contact area measuring method are applicable are those requiring data on improvement in reliability, functionality, and performance of friction-based paper feeding systems, such as office machines represented by copiers, and frictional drive systems, such as friction drives and ultrasonic motors.

In the following, the contact area measuring apparatus and the process used for measuring the contact area will be described in detail with reference to specific examples. In these examples, white polarized light interferometry is used to visualize the real contact area.

FIG. 1 shows a system for measuring a real area of contact based on a stereo microscope. The measuring system is formed of a typical stereo microscope, which is the heart of the system, and a coaxial optical fiber illuminator. The process used for measuring the real contact area is as follows: First, white light from a halogen lamp 1 is introduced through a light guide 2 formed of optical fibers to a polarizer 3, where the light is converted into linearly polarized light. Then, the light is incident on a beam splitter 8, where the light is split into two beams. One of the light beams is directed toward a specimen 7, and the other light beam is directed toward an analyzer 9. Since the analyzer 9 is rotated relative to the polarizer 3 so that the phase is shifted by an angle of 90 degrees, the light cannot pass through the analyzer 9.

The light directed toward the specimen 7 passes through a lens 4 and then a quarter-wave plate 5, where the light is converted into circularly polarized light, part of which is reflected off the lower surface of a glass plate 6 and the remainder is reflected off the specimen 7. The light reflected off the lower surface of the glass plate 6 interferes with the light reflected off the specimen 7 at the lower surface of the glass plate. The resultant interference light, when passing through the quarter-wage plate 5, is converted back into linearly polarized light, passes through the beam splitter 8, and enters the analyzer 9. Since the phase of the interference light is shifted from that of the white light having passed through the polarizer 3 by an angle of 90 degrees, the interference light can pass through the analyzer 9. The interference light then passes through a lens 10, is detected by a color image sensor 11, and produces an image having relatively strong contrast. In the present apparatus, a digital camera (Nikon CoolPix 4500 or Victor KY-F550) was used as the color image sensor 11.

In what follows, an image processing section according to the present invention is described in detail. The acquired image is analyzed using suitable software. In the present example, analysis of a real contact area is made based on an intensity histogram of the interference image. Software MATLAB is used to create an intensity histogram from the acquired image. The image (640×480 or 720×480) has 8-bit (256-grayscale) intensity data for each of the three RGB (red, green, and blue) elements. The intensity histogram is created by counting the number of pixels for each of the elements. Then, the histogram created using MATLAB is analyzed by a graph analysis function of software Origin. Normal distribution fitting, which will be described later, is performed using Marquardt optimization provided in the software Origin.

In the following, the description of a test piece according to the first embodiment of the present invention is given. In the present example, a real contact area between two flat surfaces in contact with each other is approximated to point contact that occurs between a flat surface and a sphere. This approximation provides the following advantages: (1) a contact area can be clearly identified and visualized; (2) the physical properties and the shape of the test piece allow the Hertzian contact theory to be applied; and, (3) the reliability of the experimental apparatus used in a basic experiment can be evaluated.

Next, an upper test piece is described according to the first embodiment of the present invention. The upper test piece is formed of a glass plate because the upper test piece needed to be flat and transparent. In the preferred embodiment, the glass plate is made of fused quartz with 30 mm in outer diameter and 3.0 mm in thickness and had a surface roughness of 20 nm, Young's modulus of 72 GPa, and a Poisson ratio of 0.16.

A description of a lower test piece will be given as follows. In the present example, a smooth-surface lens and a rough-surface lens are used as a lower test piece. A PMMA (polymethyl methacrylate) optical lens, which excels in surface shape precision, can be compared with a lens based on the Hertzian theory. To simulate an actual surface, a roughened PMMA optical lens is also supplementally used to investigate difference between the two cases in image analysis. The roughening is performed by rolling the lens on a 1500# emery sheet so that the irregularities thereof are transferred onto the lens. In this embodiment, each of the smooth-surface lens and the rough-surface lens is 10.0 mm in outer diameter and 23.0 mm in radius of curvature and had Young's modulus of 3.3 GPa and a Poisson ratio of 0.32. The contact area measuring apparatus of the present invention further includes a normal force loading mechanism for loading a normal force between the glass plate and the test piece.

The processing performed on an acquired image will be described in detail in what follows. Information on the intensity of a captured image includes not only information on a contact surface and the vicinity thereof obtained by using optical interferometry, but also may include information unnecessary for the analysis of the contact surface. Examples of the unnecessary information may include unevenness in illumination illuminance and scratches on the glass surface.

To eliminate such unnecessary information, "background correction" for correcting unevenness in illumination illuminance is carried out as preprocessing in the image analysis. The lower test piece is displaced vertically downward so that the glass plate is not in contact with the lower test piece and a space approximately ranging from 30 to 40 μm is created. The distance described above is large enough to not produce interference fringes, whereby an image containing only the light reflected off the lower glass surface can be obtained. An image of the real contact area is then captured at the same magnification. The unevenness in illuminance is canceled by subtracting the intensity of one of the two images from that of the other on a pixel basis. An intensity of 125 is added to ensure that the resultant intensity after the computation described above is not negative. As a result, the mode of the intensity of the background of the captured image has an intensity of approximately 125. The background correction thus solves the problem of unevenness in illuminance.

Although low-coherency white light interferometry is used in the present example, the intensity of only one of the elements described above is used in intensity analysis. The G element is used in the above-described computation. The present inventor also conducted a study on which one of the RGB elements is appropriate for the analysis. Performing the background correction on each of the RGB elements followed by creating an intensity histogram showed that the G element provides the narrowest distribution width and the highest sensitivity of the three. The following analysis is therefore made by using the intensity of the G element.

Figure 2:
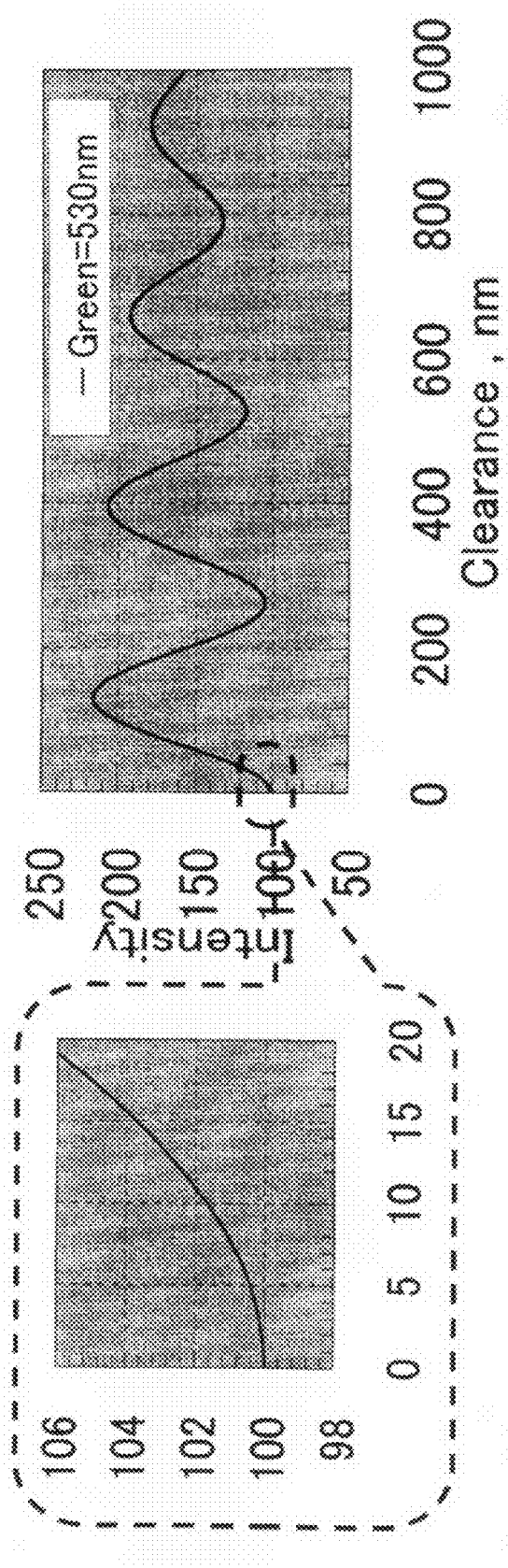
FIG. 2 shows the relationship between intensity and clearance.

Next, a description of relationship between the intensity and the distribution thereof versus the clearance, described above, are given. The equation shown in FIG. 2 can approximate the intensity of the interference light (I) produced in two-beam interferometry and provide the relationship between the intensity of the interference light (I) and the clearance. The curved graph in FIG. 2 shows the relationship between the intensity and the clearance that is derived from a two-beam interferometry theory using a low-coherency white light (G element). Since a portion where there is no clearance corresponds to a real contact area, a real contact area can be determined by extracting a region having the optical intensity (100 in this example) of a portion where there is no clearance.

Figure 3:
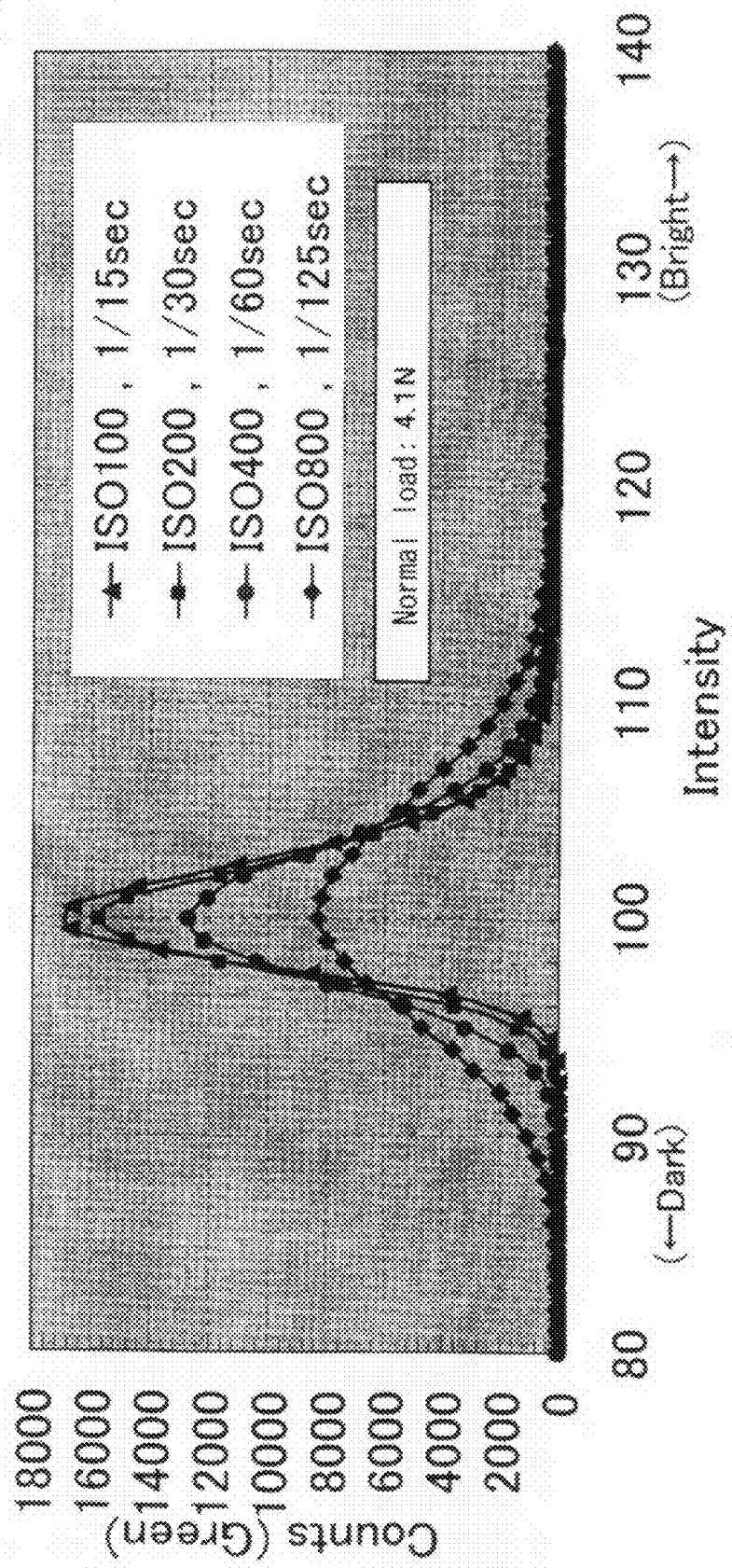
FIG. 3 shows how ISO sensitivity affects the spread of an intensity histogram.

In the theoretical curve of the optical interference intensity (intensity versus clearance) shown in FIG. 2, the expected intensity value corresponding to zero clearance is 100. In actual measurement, however, the distribution of an optical intensity histogram for a real contact (Hertzian contact) region is not a step function, as shown in FIG. 3. Conceivable reasons for this are that (1) the CCD produces noise, which typically follows a normal distribution, and (2) (RGB) color filters placed in front of the CCD do not pass exact desired representative wavelengths but have certain bandwidths that pass broad wavelengths to some extent.

In the following, the effect of how the ISO sensitivity of the camera affects an interference fringe intensity histogram will be discussed. FIG. 3 shows exemplary intensity histograms of interference images acquired under the same contact conditions (smooth-surface lens), but different ISO sensitivities of the camera are used in this example. The explanatory notes in FIG. 3 describe ISO sensitivities having been set and shutter speeds for proper exposure. Please note that the aperture is set to a fixed value. FIG. 3 shows that the intensity distribution becomes steeper as the ISO sensitivity decreases. A conceivable reason for this is that higher sensitivity causes the CCD to produce more noise. Since the width of the intensity distribution changes with the ISO sensitivity of the camera as shown in FIG. 3, the threshold for binarization used to extract the real contact area changes accordingly.

Figure 4:
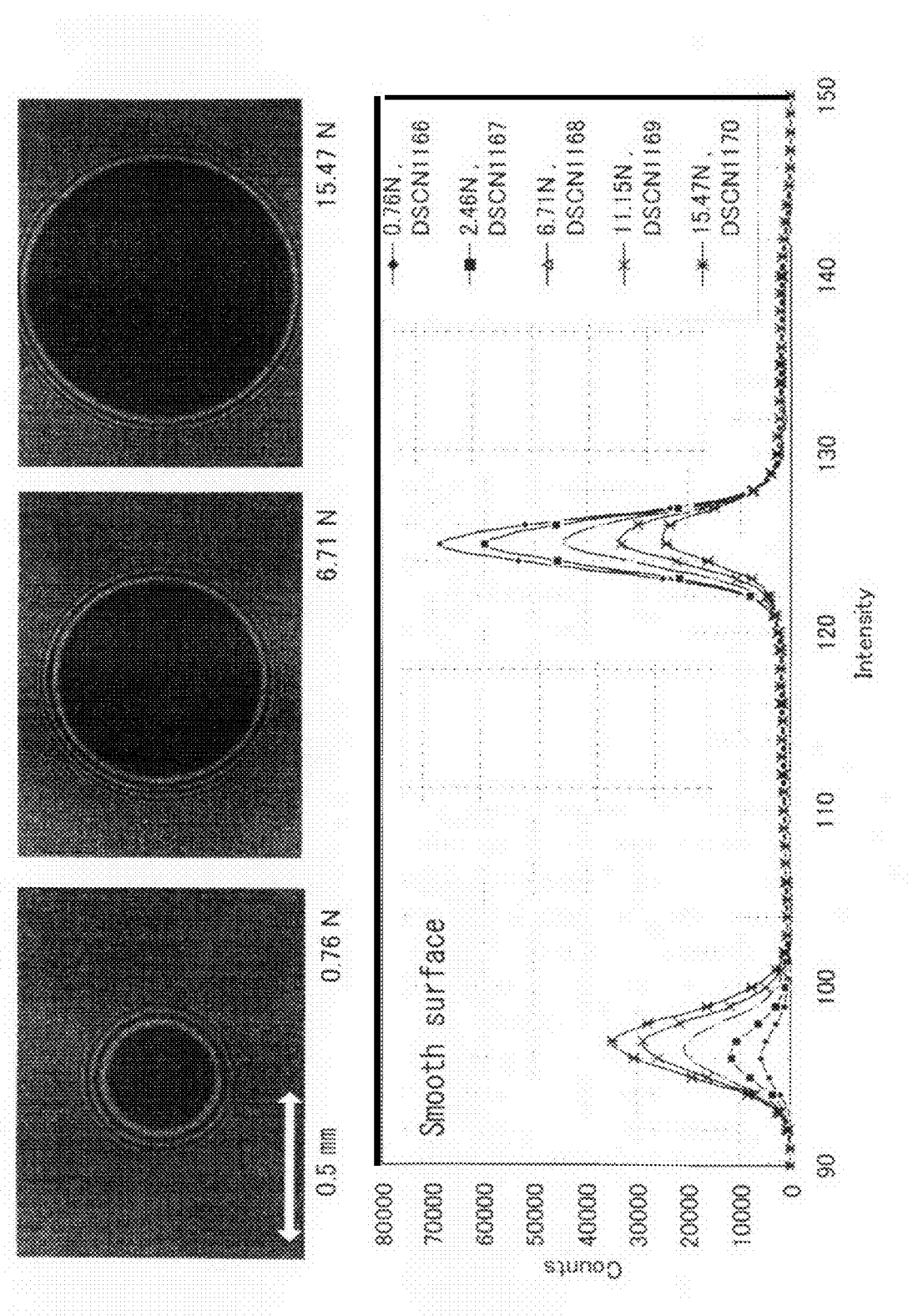
FIG. 4 shows exemplary captured images and histograms [PMMA smooth-surface lens]
Figure 5:
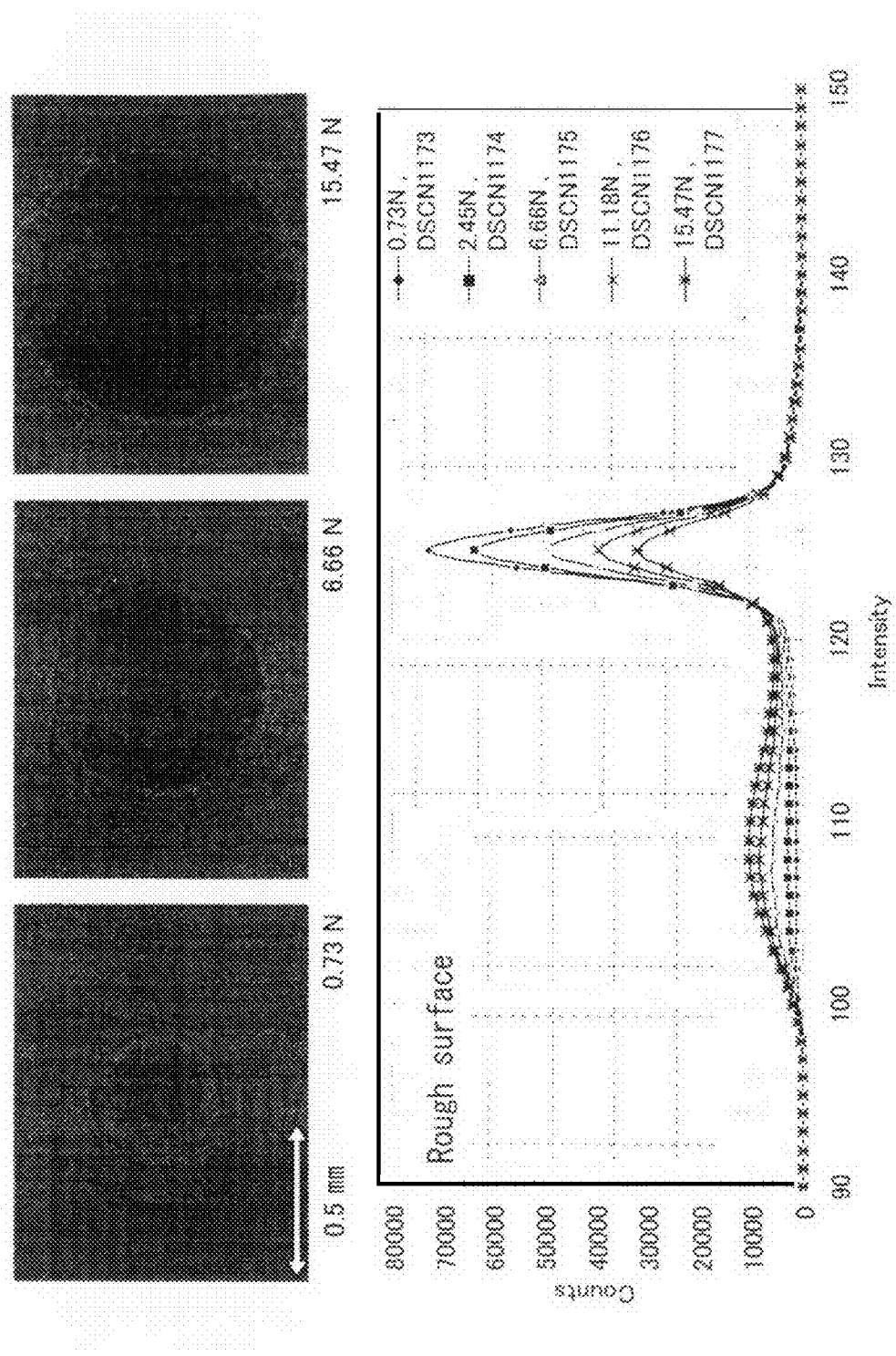
FIG. 5 shows exemplary captured images and histograms [PMMA rough-surface lens]
Figure 6:
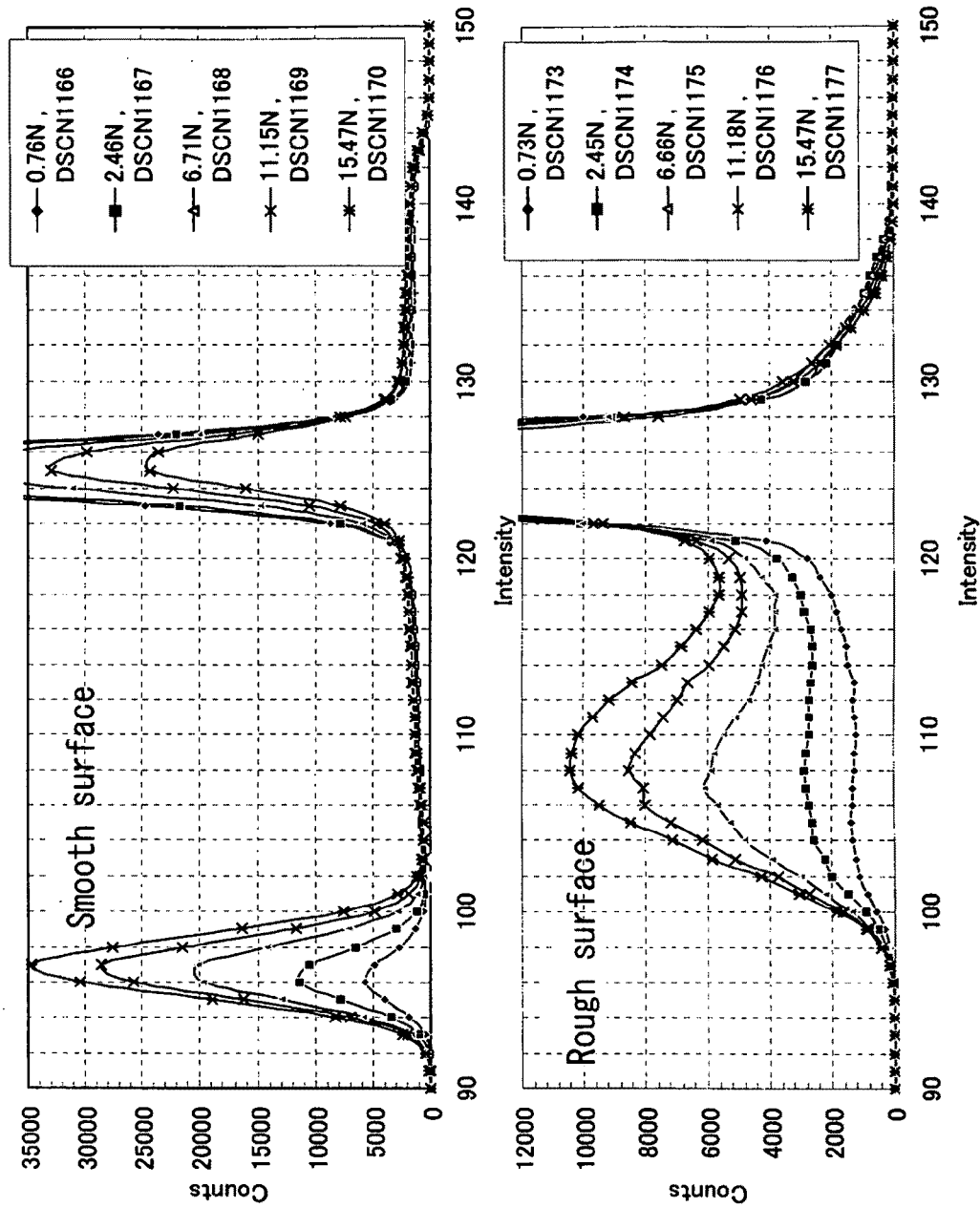
FIG. 6 shows enlarged contact portions of the smooth-surface and rough-surface histograms.

FIGS. 4 to 6 show exemplary histograms for specimens having the same shape and material but having smooth and rough surfaces. FIG. 4 shows intensity histograms obtained when the specimen is a smooth-surface lens. The photographs in FIG. 4 are captured images of the smooth-surface lens. Looking at the low-intensity side of each of the distributions that corresponds to a contact area, one can see that the intensity of the peak remains substantially unchanged as the load increases, but that the peak count and the integral of the distribution increase. Each intensity histogram clearly reflects the change in the real area of contact. When the surface is smooth, the distribution clearly has two independent raised portions representing a real contact area (left) and the background (right), whereby the real contact area can be readily separated, and the area thereof can be accurately extracted.

FIG. 5 shows histograms for the rough-surface lens, and the photographs in FIG. 5 are captured images of the rough-surface lens. As in the case of the smooth-surface lens, FIG. 5 shows that the count on the low-intensity side of each of the distributions increases as the load increases. Further, since the number of pixels on the higher-intensity side of each of the peaks is greater than that on the lower-intensity side, the distribution does not have a symmetric shape with respect to the peak. In the case of the rough surface, the two raised portions overlap, and the real contact area on the left has a wide distribution width. It is therefore difficult to determine a threshold in a conventional threshold-based method, which means that it is difficult to separate the two raised portions representing the real area of contact (left raised portion) and the background (right raised area) from each other and extract a real contact area.

FIG. 6 shows enlarged contact portions of the smooth-surface and rough-surface histograms. According to this figure, the difference in surface characteristics produces a large difference in the shape of intensity histogram.

Figure 7:
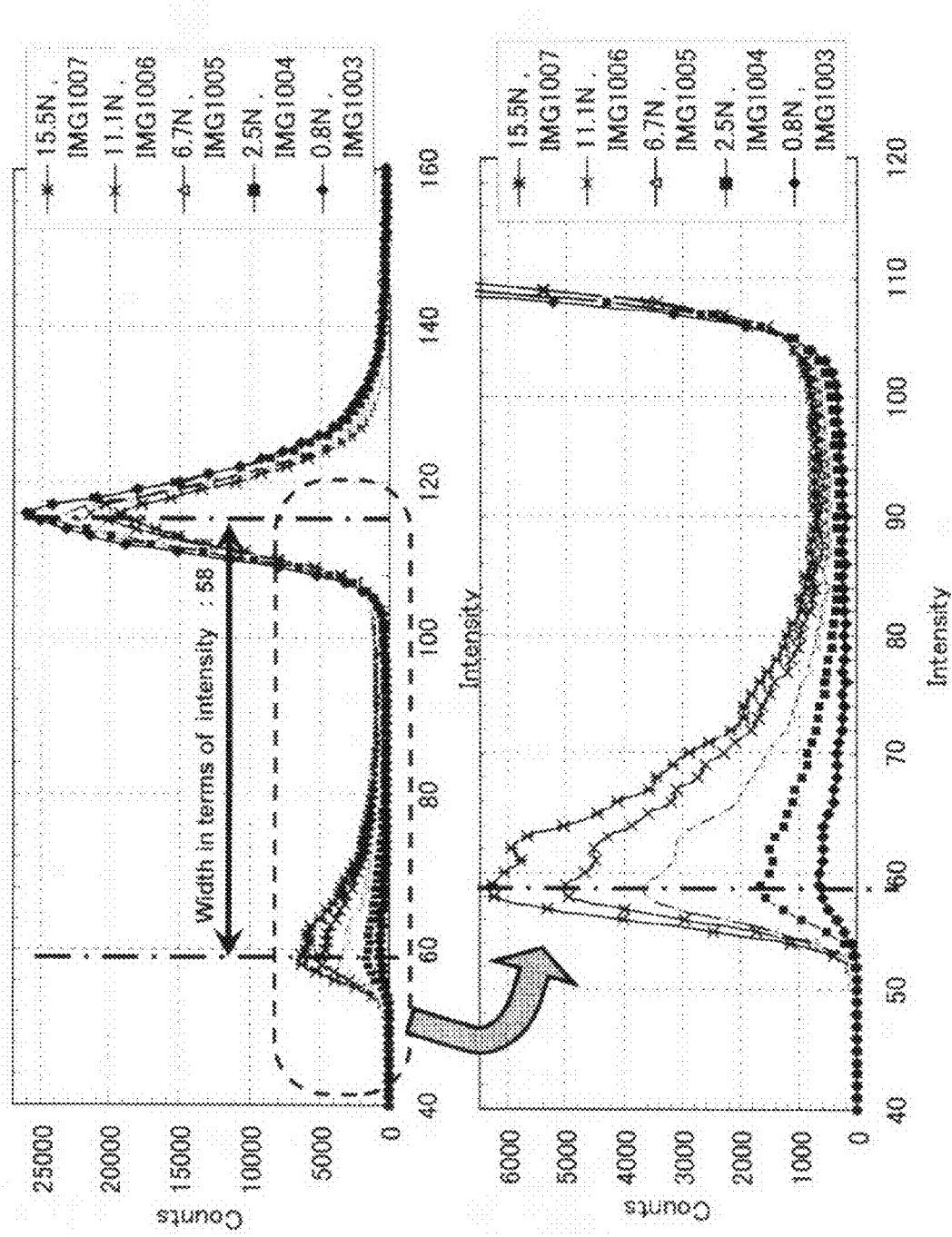
FIG. 7 shows a case where a camera having a wide dynamic range is used [rough-surface lens]

FIG. 7 shows intensity histograms for the rough-surface lens shown in FIG. 5 where a camera having a wide dynamic range is used. In the case where a camera having a narrow dynamic range is used (FIG. 5), the peak-to-peak distance in terms of intensity is 16 (=125−109). On the other hand, in the case where a camera having a wide dynamic range is used (FIG. 7), the peak-to-peak distance in terms of intensity is 58 (=116−58). This means that the wide-dynamic-range camera can record the difference in optical intensity between the two peaks produced by an object three times larger than the narrow-dynamic-range camera for the same object. That is, the difference in dynamic range can cause a difference in shape of the obtained intensity histogram. When the dynamic range is wide, the two raised portions are substantially independent from each other. This is also true in the case of rough surface, whereby a real contact area can be more readily separated. In a conventional threshold-based method, however, the characteristics of the surface and the performance of the camera cause the threshold to vary in the manner described above. It is therefore necessary to estimate an optimum threshold whenever the camera (CCD) and the contact conditions change.

A real contact area can be extracted irrespective of the threshold, the magnitude of intensity, the characteristics (dynamic range) of the camera, and other conditions when the real contact area shows a specific intensity histogram distribution pattern. Analysis based on a normal distribution is now proposed. A synthetic separation method based on typical curve adaptation is applied. That is, curve fitting is performed on an intensity histogram, assuming that the histogram is a combination of a plurality of distributions. The graph analysis software Origin is used for the subsequent analysis. In this analysis, an intensity histogram is assumed to be a combination of a plurality of normal distributions. Among the plurality of normal distributions, let a region I be the lowest-intensity normal distribution. The region I is determined in such a way that it has a peak in the vicinity of a mode of experimental values and it agrees well with experimental values on the lower-intensity side of the mode.

Figure 8:
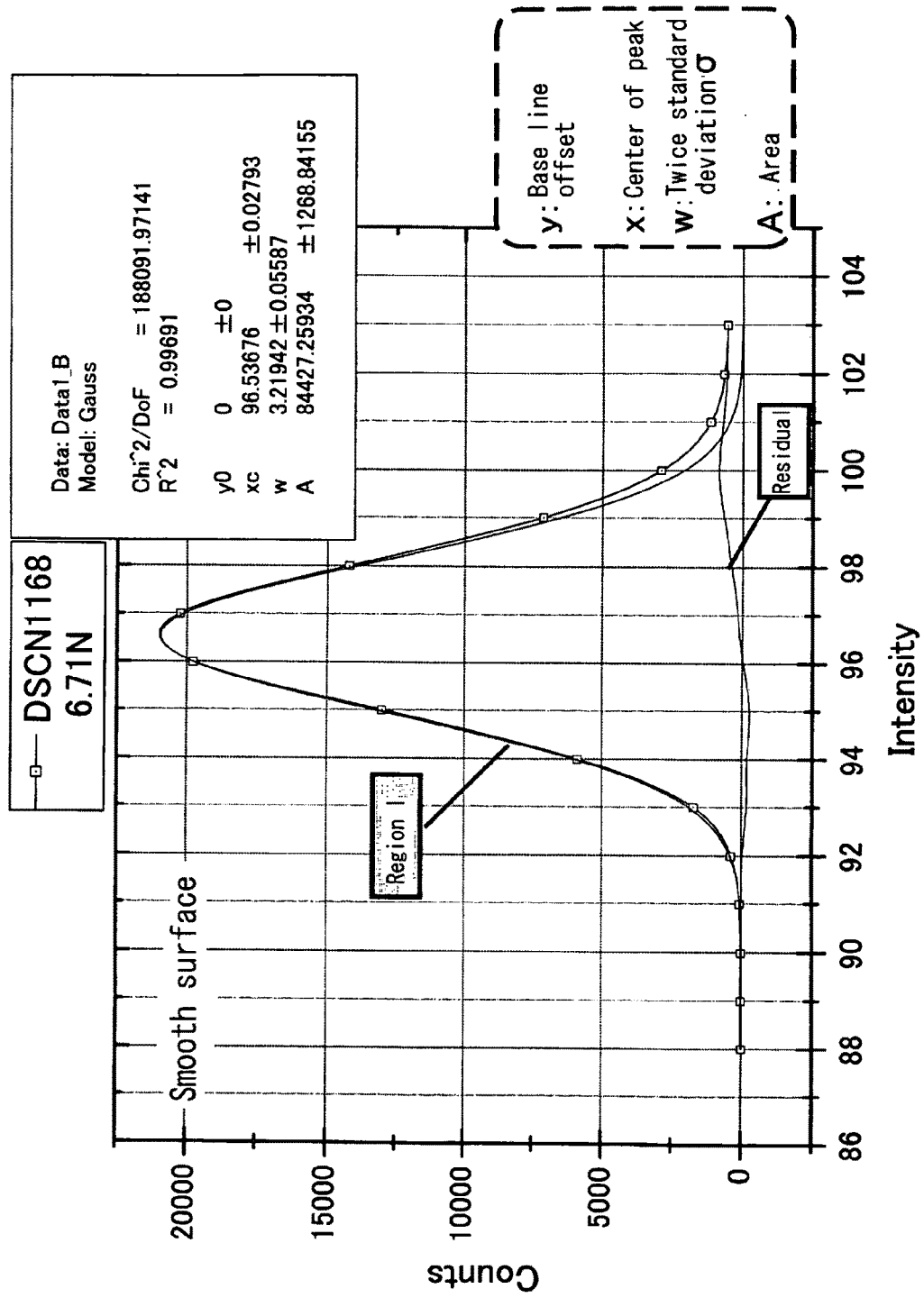
FIG. 8 shows fitting with a normal distribution I [smooth-surface lens]

FIG. 8 shows an intensity histogram distribution in an ideal Hertzian contact using a smooth-surface lens. A first raised portion on the lower-intensity side of the intensity histogram, provided that the intensity histogram has a complex normal distribution, undergoes fitting. The resultant normal distribution I fits well with the left half, which is on the lower-intensity side, and the residual is very small. The residual on the higher-intensity side (right half) is also small and the normal distribution is symmetric.

Figure 9:
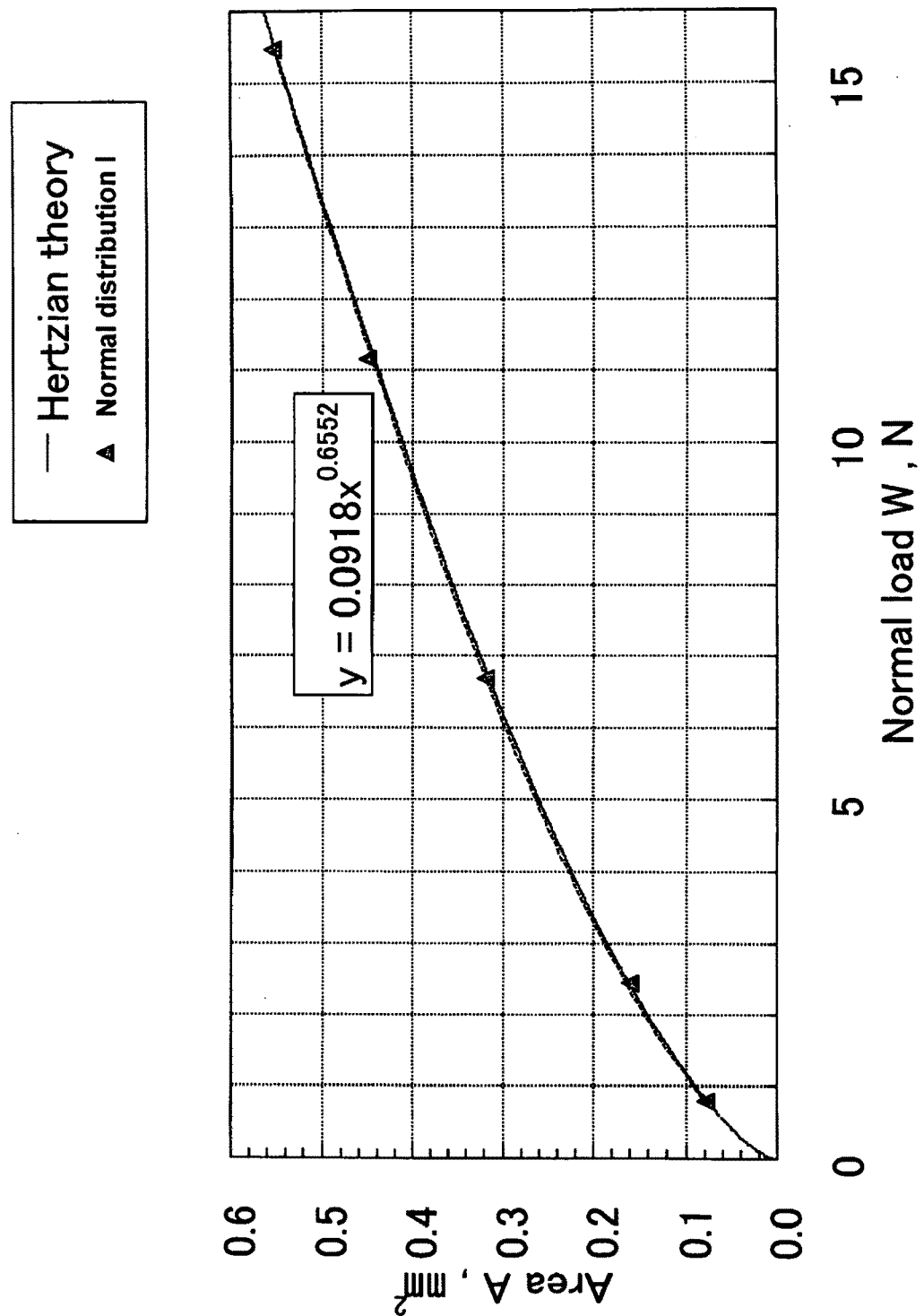
FIG. 9 shows the area of the normal distribution I and the area derived from the Hertzian theory.

FIG. 9 shows results obtained by performing normal distribution fitting for each load and converting the total count in the resultant region I into a real area (mm2). FIG. 9 also shows theoretical values derived from the Hertzian elastic contact theory for reference. FIG. 9 shows that the area of the region I coincides very well with those derived from the Hertzian theory across the range of the loads used in the experiment. It is therefore concluded that the size of the region I can be considered as that of a real contact area. Further, the ISO sensitivity and the RGB elements do not affect the results.

A conventional problem in extracting a real contact area is how to determine the threshold for binarization. In contrast, the real contact area measuring method of the present invention allows statistic measurement based on only the intensity histogram of an image without requiring a threshold for binarization.

Figure 10:
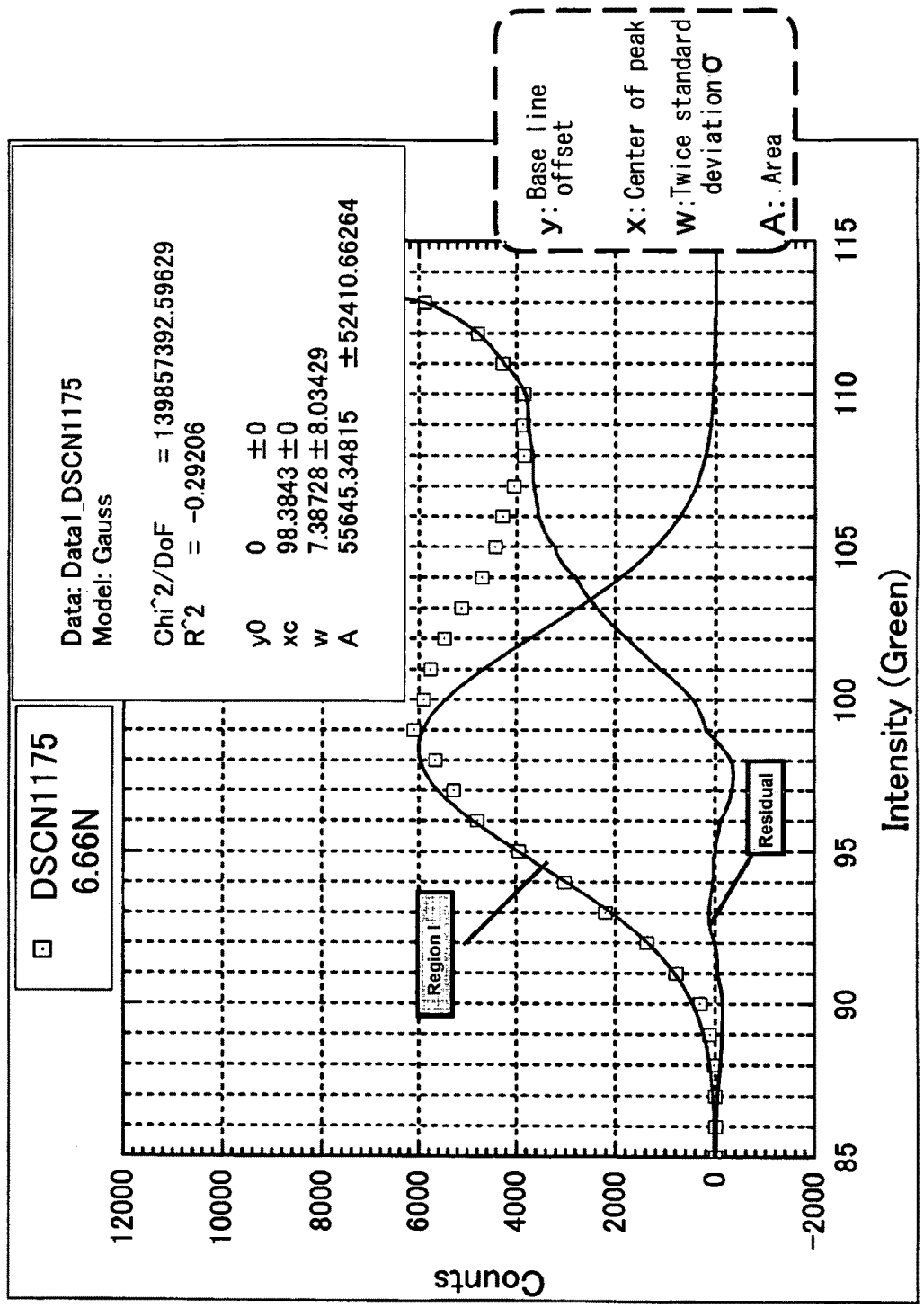
FIG. 10 shows an example of histogram region separation [rough-surface lens, when load is 6.66 N]

In the case of a rough surface, as shown in FIG. 10, it is recognized that the intensity distribution is also similar to a complex normal distribution. The normal distribution I fits well with the left half (the lower-intensity side) of a first lower-intensity side raised portion, and the residual is also small. On the other hand, the residual on the higher-intensity side (right half) is large, and the distribution is asymmetric unlike in the case of the smooth surface.

Figure 11:
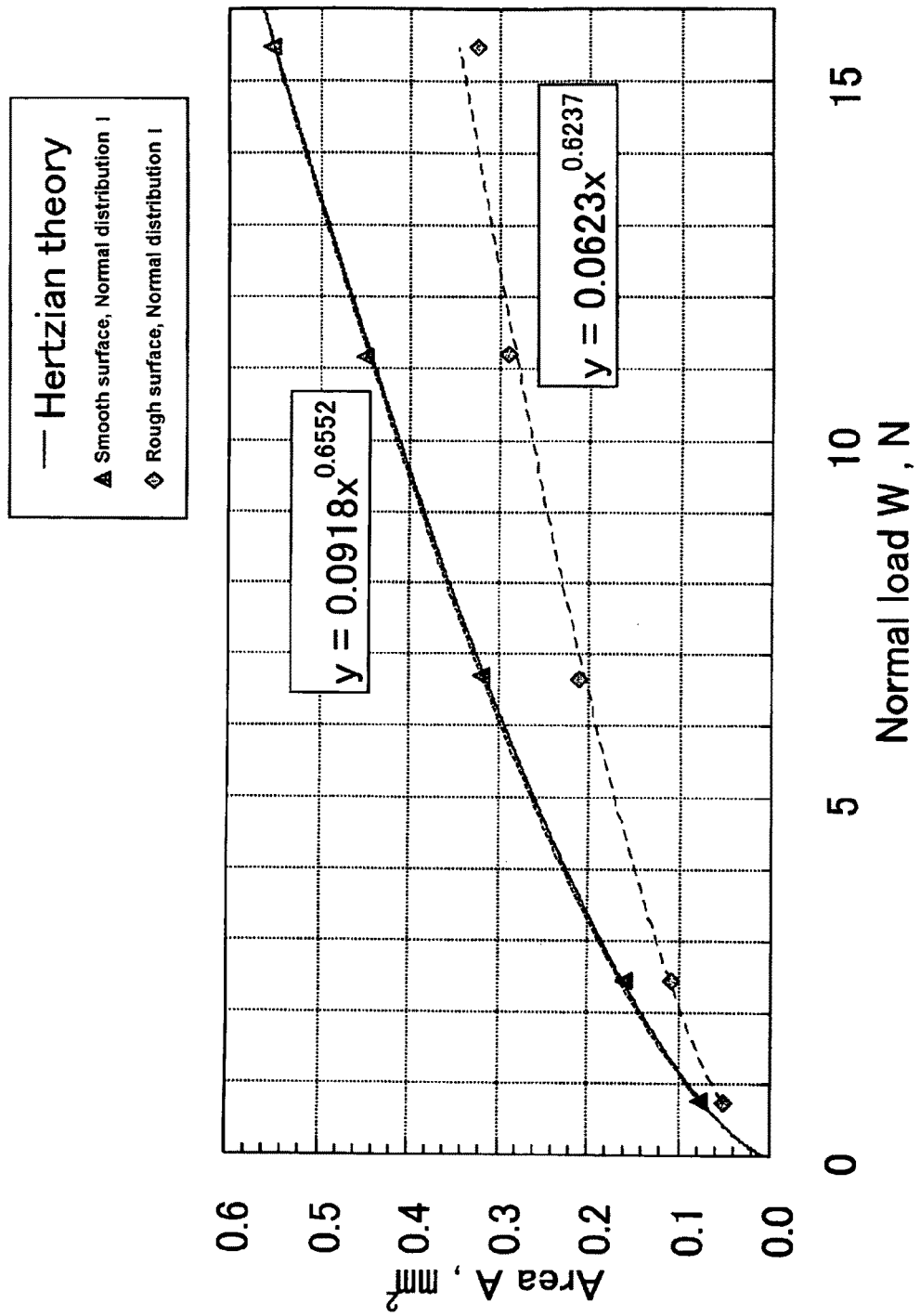
FIG. 11 shows the area of the normal distribution I and area derived from the Hertzian theory.

FIG. 11 illustrates results by assuming that the region of the normal distribution I is a real contact area and extracting the real contact area across the load range. As shown in this figure, when the surface is rough, the real area of contact can regress to a power function although it cannot be theoretically estimated.

Figure 12:
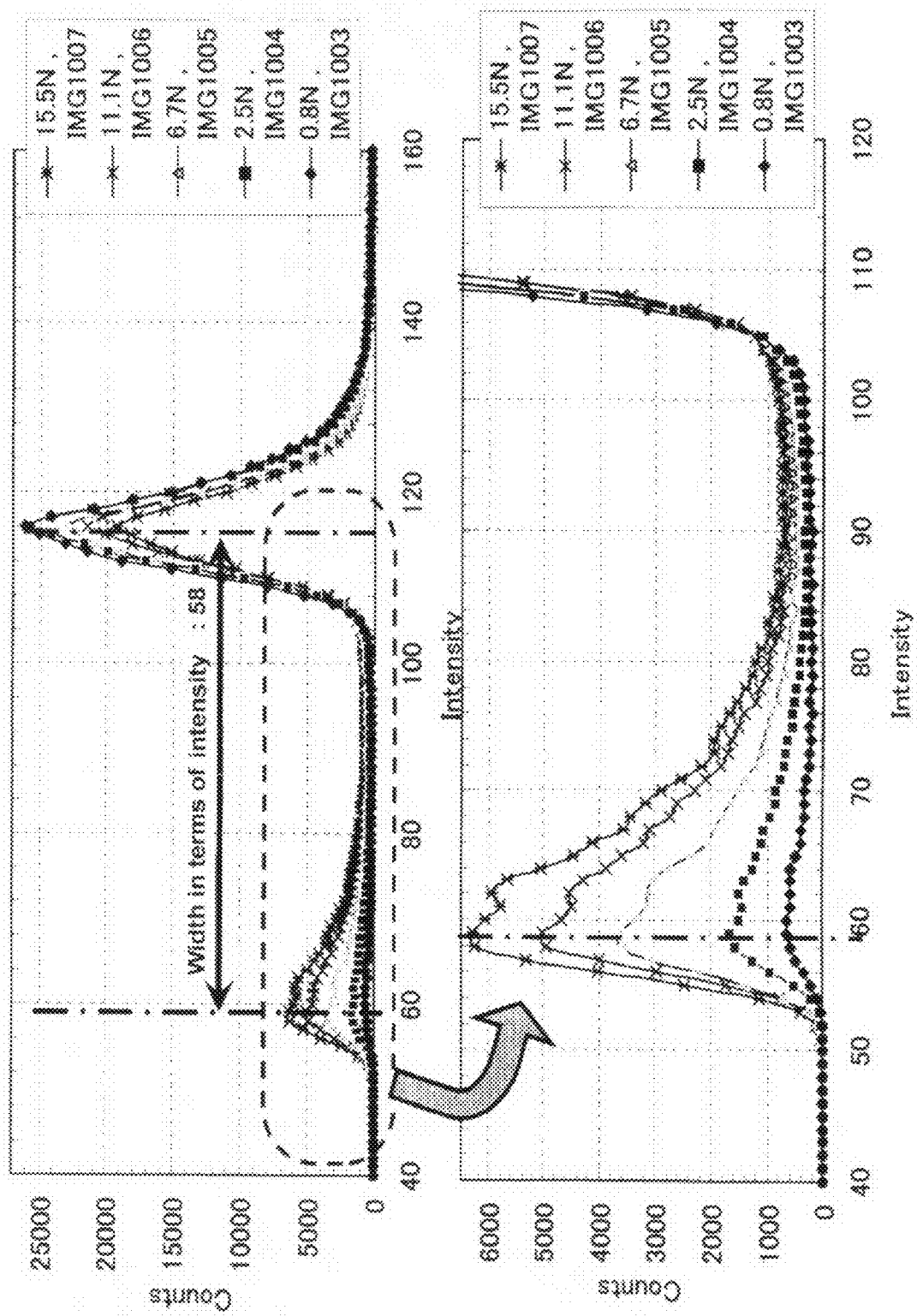
FIG. 12 shows a case where a camera having a wide dynamic range is used [rough-surface lens]
Figure 13:
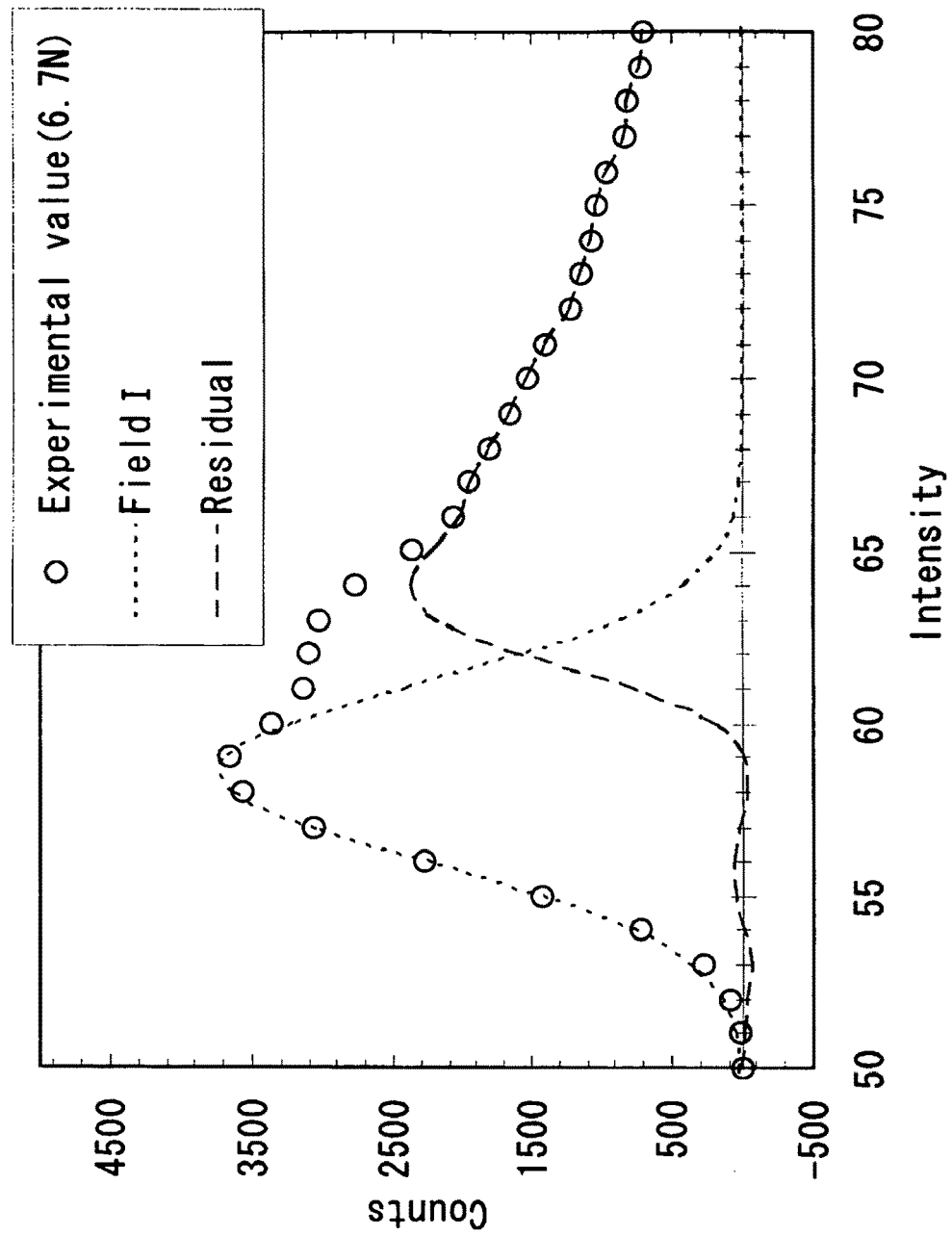
FIG. 13 shows an example of histogram region separation [rough-surface lens]
Figure 14:
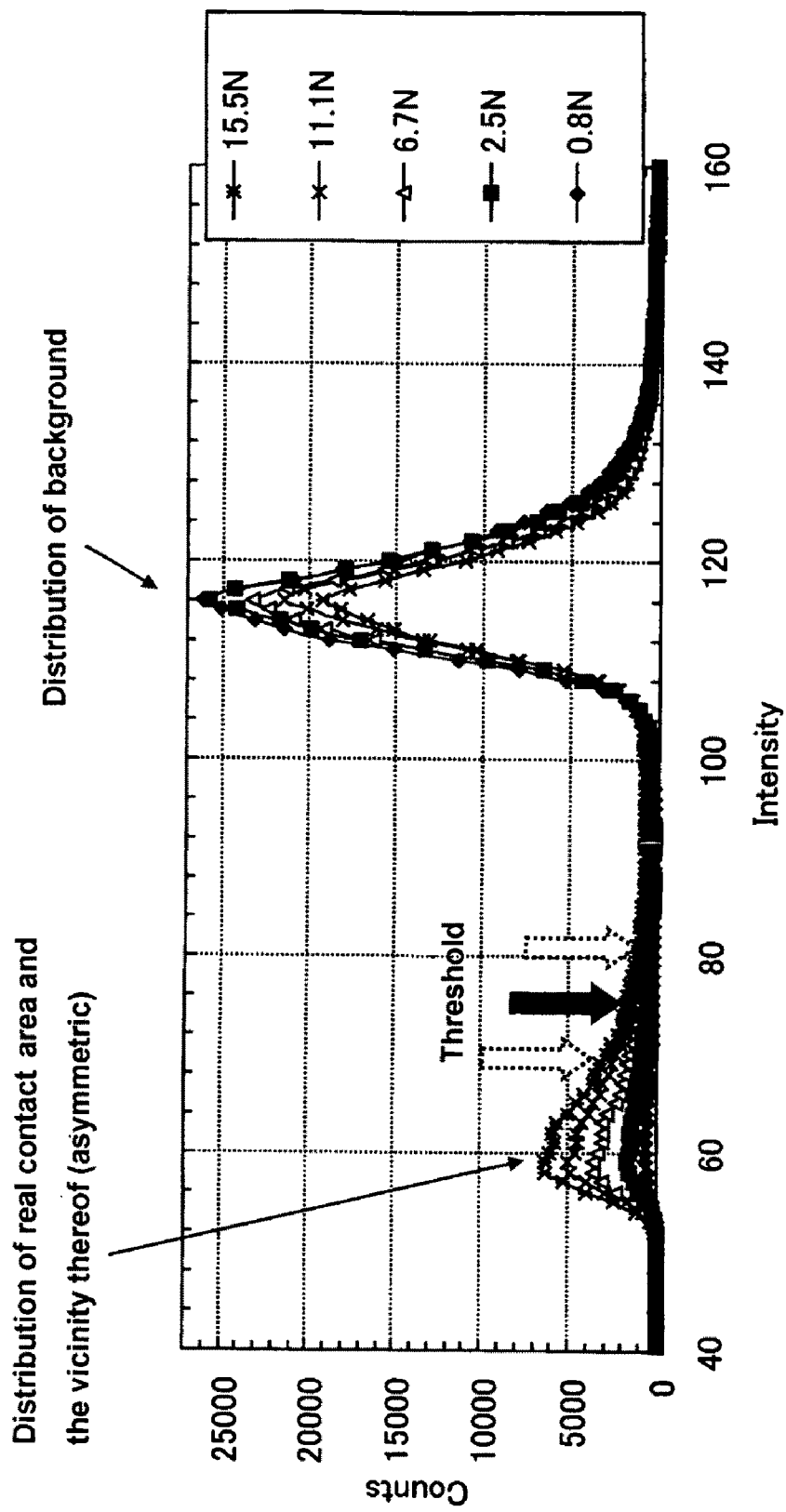
FIG. 14 shows the relationship between an intensity histogram and a threshold for binarization.
Figure 15:
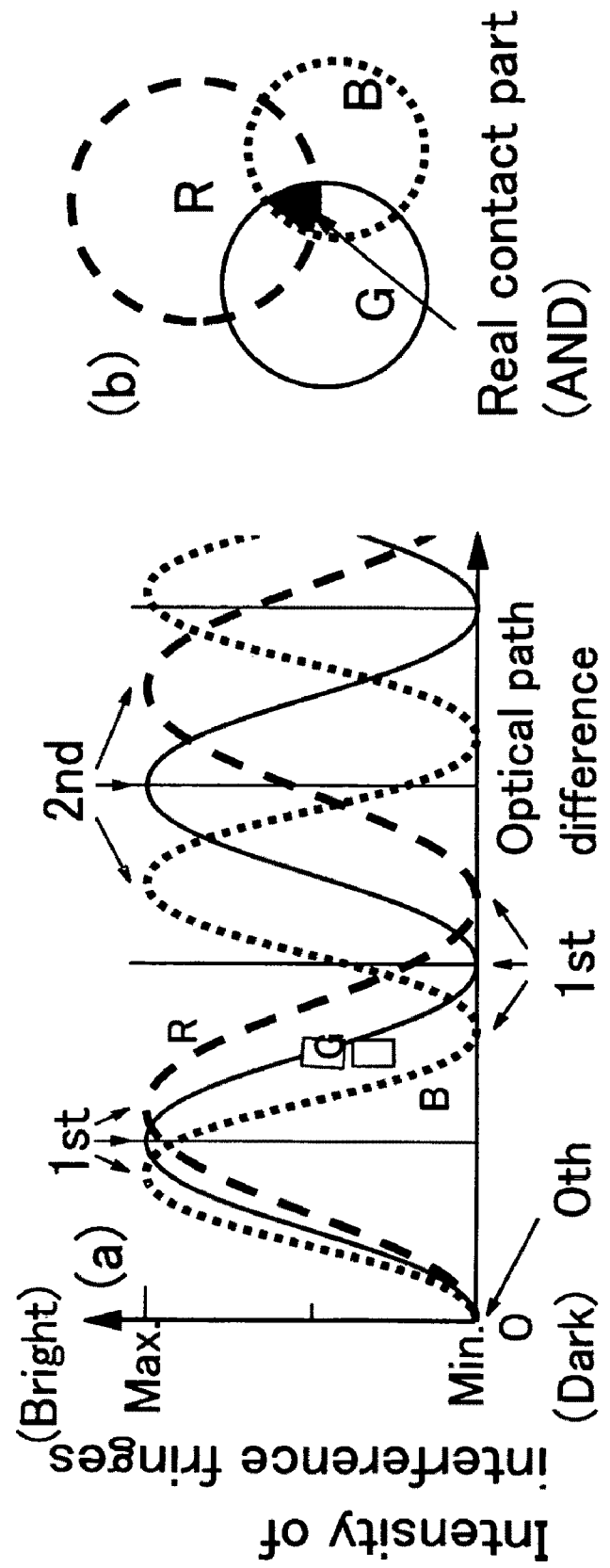
FIG. 15 shows an RGB-AND method.
Figure 16:
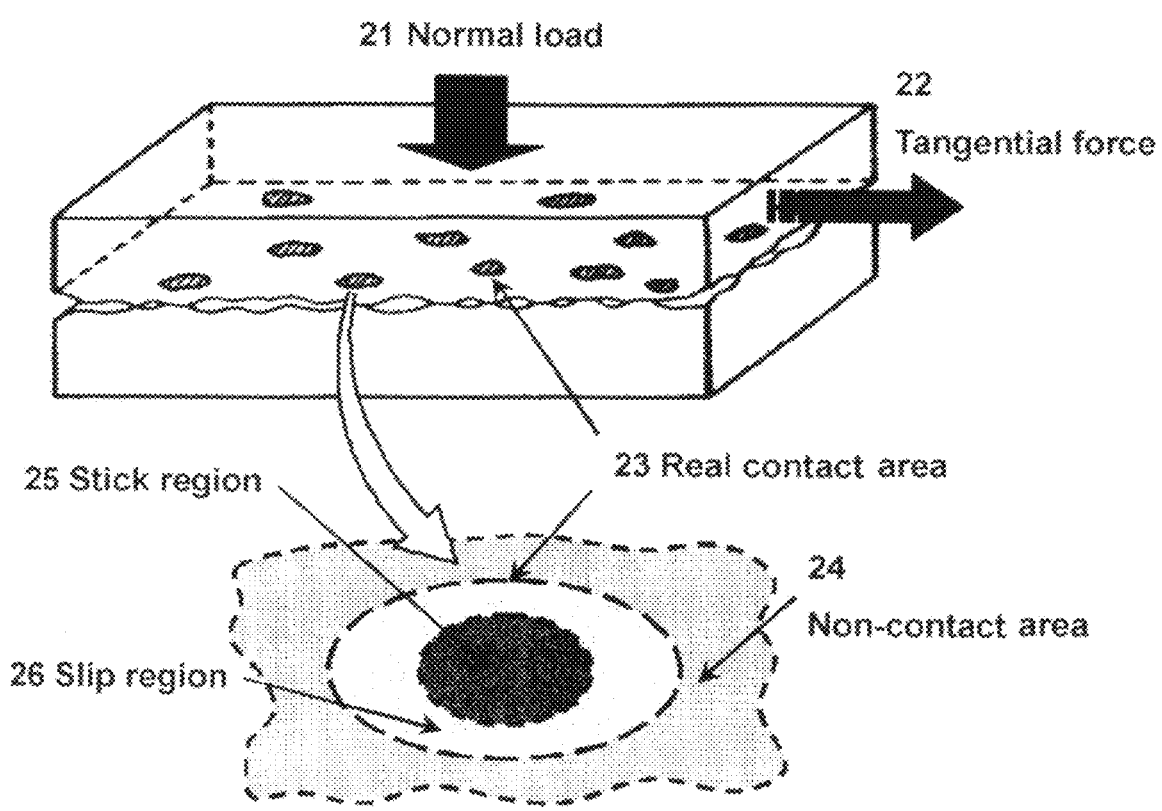
FIG. 16 shows a real contact area and a stick region.

FIG. 12 shows intensity histograms for a rough surface obtained by using a camera having a wide dynamic range as in the case of FIG. 7. The separation width from the center of the background is approximately 58 in terms of intensity, whereby first and second raised portions are readily separated. Further, complex normal distribution fitting performed on the first raised portion shows high adaptability to the lower-intensity side (left half) of the first raised portion, which is steep, as shown in FIG. 13. On the other hand, one can see that the distribution on the higher-intensity side (right half) is a wide, stepwise distribution. Use of a camera having a wide dynamic range is thus effective in performing more accurate normal distribution fitting, which is important to the invention.

As described above, the invention provides the following advantageous effects, as compared with the conventional methods:

(1) An intensity histogram of a low-coherency image is acquired. The distribution on the lowest-intensity side undergoes normal distribution fitting. A region that fits with a normal distribution is considered as a real contact area and extracted. It is therefore unnecessary to specify an intensity threshold for binarization.

(2) Since analysis is made based on statistic information on an entire contact surface (the shape of the distribution of an interference image intensity histogram) even when camera and imaging conditions change, the present method is robust against unevenness in illumination, scratches and dust, and other local variations.

(3) The accuracy in extracting a real contact area is improved by using a camera having a wider dynamic range. In a conventional threshold-based method, evaluation of a portion having a slight clearance in the vicinity of a real contact area always remains as a problem.

(4) Using white polarized light interferometry allows any material and characteristics of the contact surface to be tested (even a low-reflectance, rough surface can be evaluated).

The invention can, of course, not only be carried out by the best mode described above but also employ any other variety of configurations as long as they do not depart from the substance of the invention.

The best mode for carrying out a second aspect of the invention for the contact area measuring apparatus and the contact area measuring method will next be described.

The contact area measuring apparatus of the present invention may include a light transmissive substrate in contact with a specimen, a driving means for moving the specimen and the light transmissive substrate relative to each other, an illumination means for illuminating the light transmissive substrate with white light from the opposite side of light transmissive substrate to the specimen. The contact area measuring apparatus further includes an interference image acquisition means for acquiring an interference image produced by the light reflected off the specimen and the light reflected off the light transmissive substrate, an intensity histogram creation means for creating an intensity histogram from information on the intensity of the interference image, and an image analysis and computation means for calculating an intensity difference histogram from the intensity histogram.

The contact area measuring method of the present invention includes the steps of; placing a specimen on a light transmissive substrate so that they come into contact with each other, moving the specimen and the light transmissive substrate relative to each other, illuminating the light transmissive substrate with white light from the opposite side of the light transmissive substrate to the specimen, acquiring an interference image produced by the light reflected off the specimen and the light reflected off the light transmissive substrate, creating an intensity histogram from information on the intensity of the interference image, and calculating an intensity difference histogram from the intensity histogram.

The interference image acquisition means of the contact area measuring apparatus acquires an interference image and information on the intensity of the interference image. White polarized light interferometry, which does not depend on the material of the specimen or the surface characteristics thereof, is used to acquire an image that visualizes a contact area. More specifically, a stereo microscope and white polarized light interferometry are used to visualize a minute clearance produced at the interface between the light transmissive substrate and the specimen pressed thereagainst. Further, a video camcorder is used to acquire an interference fringe image produced at the periphery of the contact area. Low coherency of the white light and resultant low intensity of higher-order dark interference fringes, which are not related to a real contact area, allow only the real contact area to be readily extracted. The light transmissive substrate can, for example, be made of glass, sapphire, or polycarbonate.

The intensity histogram creation means of the contact area measuring apparatus forms separate RGB intensity information from the information on the intensity of the interference image and creates a G-intensity histogram. When a color video camcorder is used, separate RGB intensity information is formed by using image processing software to process an acquired image, and then an intensity histogram is created only from the information on the intensity of the G-image. The reason for this is that the G element has the highest sensitivity. It is noted that the object of the invention can be achieved by using an R-intensity histogram or a B-intensity histogram as well as the G-intensity histogram.

The image analysis and computation means of the contact area measuring apparatus calculates an intensity difference histogram from the intensity histogram and determines the region of the intensity difference histogram that has positive values. A still image (tangential force coefficient $\phi=0$) is used as a reference to successively compute the intensity histogram difference between an arbitrary image ($\phi$=arbitrary value) and the reference image and also to determine a point where the intensity difference histogram changes from positive to negative. The region having the positive values is determined as a decrease in a stick region in the real contact area.

In an alternative embodiment, the contact area measuring apparatus includes a light transmissive substrate in contact with a specimen, a driving means for moving the specimen and the light transmissive substrate relative to each other, an illumination means for illuminating the light transmissive substrate with white light from the opposite side of the light transmissive substrate to the specimen, an interference image acquisition means for acquiring an interference image produced by the light reflected off the specimen and the light reflected off the light transmissive substrate, and an image analysis and computation means for using information on the intensity of the interference image as a tracking marker.

In an alternative embodiment, the contact area measuring method includes the steps of placing a specimen on a light transmissive substrate so that they come into contact with each other, moving the specimen and the light transmissive substrate relative to each other, illuminating the light transmissive substrate with white light from the opposite side of the light transmissive substrate to the specimen, acquiring an interference image produced by the light reflected off the specimen and the light reflected off the light transmissive substrate, and using information on the intensity of the interference image as a tracking marker.

The interference image acquisition means of the contact area measuring apparatus is configured as described above in the first embodiment.

The image analysis and computation means of the contact area measuring apparatus calculates a velocity vector by using the information on the intensity of the interference image as a tracking marker.

The contact area measuring apparatus and the contact area measuring method of the present invention are applicable to technical fields requiring data on prototype/technology developments that are directly related to: development and performance evaluation of frictional materials used for brakes, clutches, and other components. They are also applicable to technical fields requiring data on improvement in contact/friction maintenance between surface and tires, shoe soles, and other products. Other fields to which the contact area measuring apparatus and the contact area measuring method are applicable are those requiring data on improvement in reliability, functionality, and performance of friction-based paper feeding systems, such as office machines represented by copiers, and frictional drive systems, such as friction drives and ultrasonic motors. Still other fields to which the contact area measuring apparatus and the contact area measuring method are applicable are those requiring data supply for controlling a grip of a robot hand or data supply to a device for presenting haptic information used to judge whether or not "an object will slip", the device used, for example, in functional improvement rehabilitation after any of the fingers and arms of a person suffers from a functional disorder.

Figure 17:
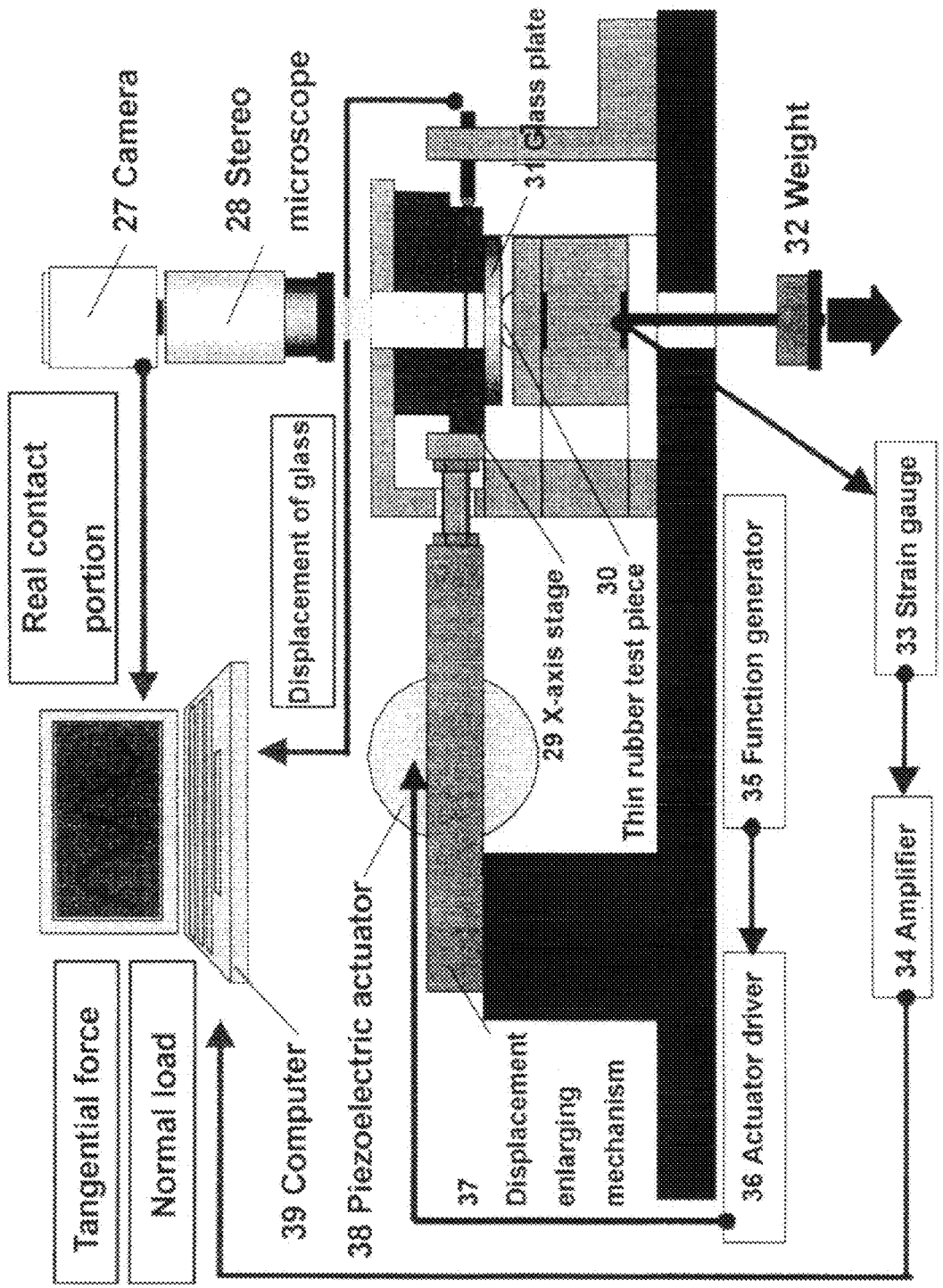
FIG. 17 is a schematic view of an experimental apparatus.

In what follows, the contact area measuring apparatus and the contact area measuring method will be described with reference to specific examples. First, the experimental apparatus used in the present examples will be described. FIG. 17 shows a schematic diagram of an embodiment of the experimental apparatus used in the present example. The present apparatus can be broadly grouped into a reciprocating friction testing section and a visualizing system section. A driver of the reciprocating friction testing section can be changed to achieve large displacement (displacement of ±400 μm) by incorporating a displacement enlarging mechanism. A vibration generation voltage waveform produced by a function generator 35 is inputted to a piezoelectric actuator 38 via an actuator driver 36 and expands or contracts the piezoelectric actuator 38. A displacement enlarging mechanism 37 is connected to a glass plate holder, and a glass plate 31 makes reciprocating motion in the horizontal direction. The amplitude of the displacement of the glass plate 31 is measured with a displacement meter, and a normal force and a tangential force applied to a contact surface are measured with strain gauges attached to a parallel plate spring. The measured analog values are converted into digital values and recorded in a computer 39. At the same time, the visualizing system section, using a stereo microscope 28, records video images captured with a three-CCD color video camcorder 27.

In the following, each of the above-mentioned portions of the experimental apparatus will be explained individually in detail. In the present example, white polarized light interferometry is used to visualize a real contact area. A description of a measuring system using white light interferometry will be first given. The measuring system is formed of a typical stereo microscope, which is the heart of the system, and a coaxial optical fiber illuminator. The principal according to which the measurement is made may be described as follows: first, white light from a halogen lamp is introduced through a light guide formed of optical fibers to a polarizer, where the light is converted into linearly polarized light. Then, the light is incident on a beam splitter, where the light is split into two light beams. One of the light beams is directed toward a specimen, and the other light beam is directed toward an analyzer. Since the analyzer is rotated relative to the polarizer in away that the phase is shifted by an angle of 90 degrees, the light cannot pass through the analyzer.

The light directed toward the specimen passes through a lens and then a quarter-wave plate, where the light is converted into circularly polarized light, part of which is reflected off the lower surface of a glass plate and the remainder is reflected off the specimen. The light reflected off the lower surface of the glass plate interferes with the light reflected off the specimen at the lower surface of the glass plate. The resultant interference light, when passing through the quarter-wage plate, is converted back into linearly polarized light, passes through the beam splitter, and enters the analyzer. Since the phase of the interference light is shifted from that of the white light having passed through the polarizer by an angle of 90 degrees, the interference light can pass through the analyzer. The interference light then passes through a lens, is detected by a color image sensor, and produces an image having relatively strong contrast. In the present apparatus, a 3-CCD color video camcorder (Victor KY-F550) is used as the color image sensor.

Next, the drive section of the contact measuring apparatus will be described. The drive section of the present apparatus is formed of a piezoelectric actuator 38, an actuator driver 36, and a function generator 35. The function generator 35 (manufactured by Hewlett-Packard Development Company, HP33120A) sets the waveform, the frequency, and the amplitude used in the drive section, and the actuator driver 36 adjusts the bias voltage and the gain used in the drive section. The piezoelectric actuator 38 (manufactured by DENSO CORPORATION, PH22100) is a laminated type, which produces large force and excels in responsiveness. Since the piezoelectric actuator 38 is made of a piezoelectric ceramic, no electromagnetic noise or other harmful noise is advantageously produced.

Figure 18:
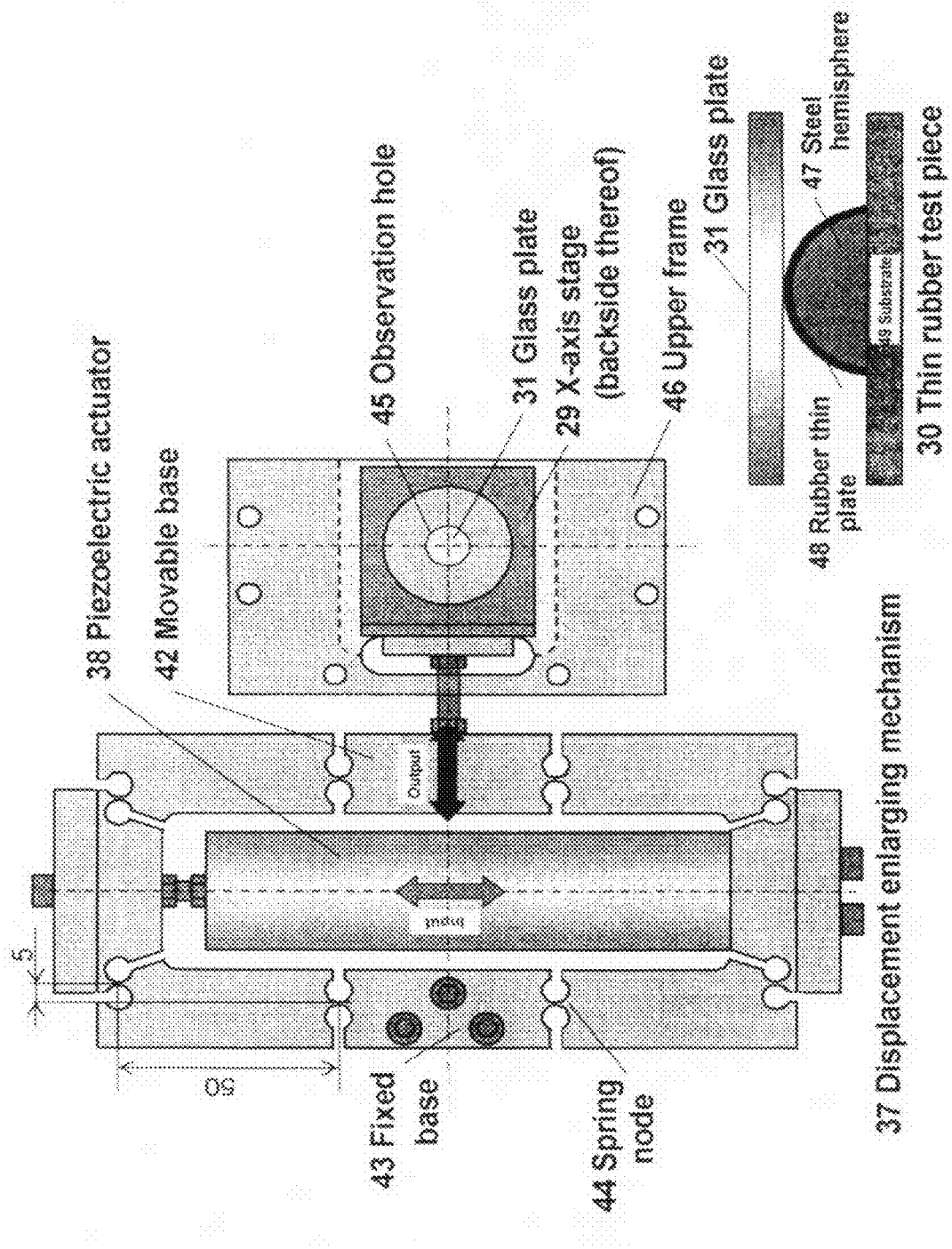
FIG. 18 is a schematic view of a displacement enlarging mechanism and a test piece.

The displacement enlarging mechanism 37 will be described as follows. The displacement enlarging mechanism 37 is a link mechanism having eight spring nodes, as shown in FIG. 18. When the piezoelectric actuator 38 is disposed at the center of the link mechanism, the link mechanism changes the direction of the expansion/contraction of the piezoelectric actuator by 90 degrees. The magnification of the expansion/contraction is determined by the ratio between longer and shorter distances between the nodes. In the specification of the present mechanism, this ratio is 5 mm:50 mm and hence the magnification is 10. The expansion/contraction of the piezoelectric actuator 38 is transferred to the glass plate 31 via the displacement enlarging mechanism 37 and under the guidance of a slider of an X-axis stage 29.

In the following, the normal force loading mechanism will be described. The normal force loading mechanism loads a normal force between the glass plate and the test piece. The normal force loading mechanism is configured in such a way that a suspended weight displaces the test piece in the vertical direction so that the normal force acting on a contact area is adjusted as appropriate.

Next, a load measuring section will be described. The measurement system of the present test apparatus measures the normal force loaded to the contact area between the glass plate and the test piece and the tangential force produced when relative motion occurs between the glass plate and the test piece. The normal force is measured with a normal force measuring gauge, and the tangential force is measured with a tangential force measuring gauge. The output from each of the normal force measuring gauge and the tangential force measuring gauge is amplified by a DC amplifier and supplied to the computer via an A/D conversion board.

Displacement measurement will be described as follows. The displacement of the glass plate is measured with a displacement meter. A differential-transformer-type displacement meter is used as the displacement meter. The output from the displacement meter is supplied to the computer via the A/D conversion board.

Then, the data recording section will be described. The present test apparatus acquires an image by using a digital video camcorder (manufactured by Victor Company, KY-F550, 720×480 pixels, 256 grayscales, shutter speed: 1/60 sec).

In what follows, the image processing section will be described. The acquired image was analyzed by software. In the present example, analysis of the real contact area is made based on the intensity histogram of an interference image. Software MATLAB is used to create the intensity histogram from the acquired image. The image (720×480) has 8-bit (256-grayscale) intensity data for each of the three RGB (red, green, and blue) elements. The intensity histogram is created by counting the number of pixels for each of the elements.

The histogram created using MATLAB software is analyzed by a graph analysis function of the software Origin. Normal distribution fitting, which will be described later, is performed using Marquardt optimization provided in the software Origin.

The description of test piece and upper test piece are exactly the same as those described in the first preferred embodiment of present invention. It should be noted that the upper test piece is not limited to a glass plate but can be a sapphire plate, an optically transparent polycarbonate or acrylic plate.

Next, a lower test piece is described according to the second embodiment of the present invention. A thin rubber test piece is used as the lower test piece because it achieves a practical surface and practical friction conditions and in expectation that low modulus of elasticity of rubber may provide greater change in the behavior of the contact surface. The thin rubber test piece is obtained by stretching a natural rubber thin plate having a thickness of 0.5 mm and bonding it onto a steel hemisphere having a radius of 5 mm. It should be noted that the lower test piece is not limited to the thin rubber test piece as described above but can be a solid rubber test piece or a wet-paper-based frictional material.

The preprocessing performed on an acquired image will be described in detail in what follows. Information on the intensity of a captured image includes not only information on a contact surface and the vicinity thereof obtained by using optical interferometry, but also may include information unnecessary for the analysis of the contact surface. Examples of the unnecessary information may include unevenness in illumination illuminance and scratches on the glass surface.

To eliminate such unnecessary information, "background correction" for correcting unevenness in illumination illuminance is carried out as preprocessing in the image analysis. The lower test piece is displaced vertically downward so that the glass plate was not in contact with the lower test piece and a space approximately ranging from 30 to 40 µm is created. The distance described above is large enough to not produce interference fringes, whereby an image containing only the light reflected off the lower glass surface can be obtained. An Image of the real contact area is then captured at the same magnification. The unevenness in illuminance is canceled by subtracting the intensity of one of the two images from that of the other on a pixel basis. An intensity of 125 was added to ensure that the resultant intensity after the computation described above is not negative. As a result, the mode of the intensity of the background of the captured image has an intensity of approximately 125. The background correction thus solves the problem of unevenness in illuminance.

Although low-coherency white light interferometry is used in the present example, the intensity of only one of the elements described above is used in intensity analysis. The present inventor also conducted a study on which one of the RGB elements is appropriate for the analysis. Performing the background correction on each of the RGB elements followed by creating an intensity histogram showed that the G element provides the narrowest distribution width and the highest sensitivity of the three. The following analysis is therefore made by using the intensity of the G element.

Next, data acquisition in a slippage initiation process will be described. The present inventor conducted an experiment to study how a stationary state transitions to macroscopic slippage when a tangential force is applied, that is, a slippage initiation process. The experiment is conducted under the conditions of no lubrication and a normal load of 2.5 N.

Figure 19:
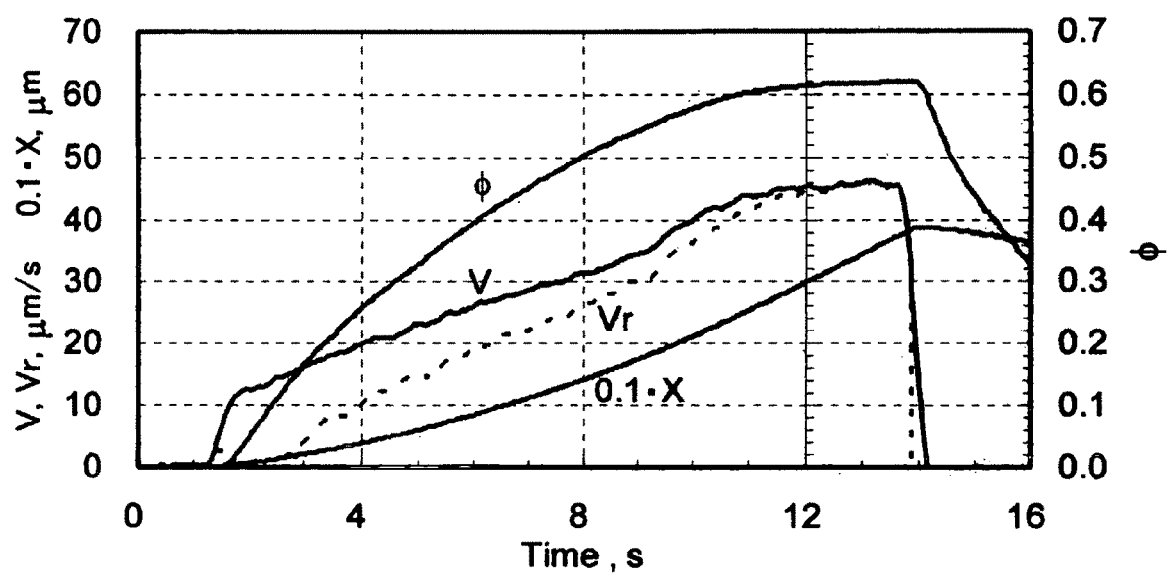
FIG. 19 is a time diagram in a slippage initiation process.
Figure 20:
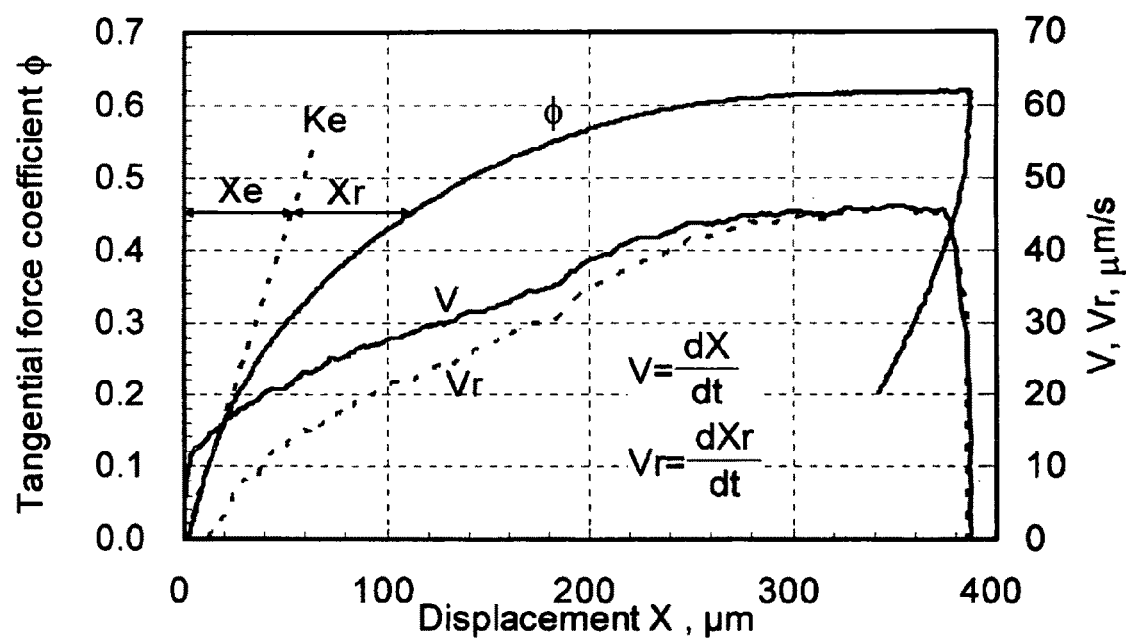
FIG. 20 is a diagram showing the relationship of a tangential force coefficient φ and a velocity V versus a displacement X in the slippage initiation process.

FIGS. 19 and 20 are, respectively, a time diagram and a diagram showing the relationship of a tangential force coefficient φ and a velocity V versus a displacement X in the slippage initiation process. The diagrams are obtained by applying a voltage having a triangular waveform and recording results until the displacement reached approximately 400 µm. The velocity V, at which the glass plate is driven, is determined at every moment by performing 19-point smoothing/differentiation computation [5] based on polynomial adaptation on measured displacement data. The AD conversion speed is set to 33.3 samples/sec.

In FIG. 19, the horizontal axis represents the measurement time from a measurement start point and the vertical axis represents the tangential force coefficient φ, the glass plate displacement X (scaled down to 1/10), and the velocity V. The value φ is obtained by dividing the tangential force by the normal force. FIG. 19 shows that the glass plate started being driven at a measurement time of approximately 1 second; the glass plate displacement direction is reversed at approximately 14 seconds (when X is 380 µm) since X, φ, and V started to change; and the directions of the graphs X, φ, and V are changed and oriented rightward and downward. In the present example, the study is conducted on the "slippage initiation process," which occurred in the section from approximately 1 second described above to 14 seconds. Although a voltage having a triangular waveform is applied, the speed at which the glass plate is driven was not constant. The reason for this is a nonlinear hysteresis phenomenon in the expansion/contraction process of the piezoelectric actuator 38.

FIG. 20 is similar to FIG. 19 but differs therefrom in that the temporal term is eliminated from the data on the tangential force coefficient φ, the glass plate displacement X, and the velocity V and the horizontal axis represents the displacement X. FIG. 20 shows a process in which φ and V increase as the glass plate is displaced from the origin of the horizontal axis in the positive direction and the directions of the graphs φ and V are then reversed. The stationary state transitions to the macroscopic slippage via a minute slippage occurrence section where a stick region and a slip region coexist. An elastic deformation line (Ke=0.021 N/µm) shown in the φ-X diagram represents the gradient in a first 20-µm section. An elastic displacement Xe is produced in this section, but a relative displacement (hereinafter referred to as minute slippage displacement) Xr along the contact interface is zero. Therefore, when the total displacement is called X, the minute slippage displacement is represented by Xr, which essentially represents the behavior in the slippage initiation process [6].

A minute slippage velocity Vr shown in FIG. 20 is the velocity of Xr and calculated by using the same method as the one used to calculate the velocity V. Since a measured displacement X is the displacement of the glass plate driven by the piezoelectric actuator, the relationship between the tangential force (that is, tangential force coefficient) and the displacement of the glass plate is expressed by a sheared linear spring when no slippage occurs between the glass plate and the rubber test piece (stick state). This state is observed in the initial 20-µm section. Therefore, only the elastic displacement Xe linearly increases, but the minute slippage displacement Xr remains zero. Assuming that a spring element and a slip element are serially connected along the contact surface, the minute slippage displacement Xr is added to the total displacement X when the tangential force increases and causes slippage.

The minute slippage velocity Vr is obtained by differentiating the minute slippage displacement Xr with respect to time. The difference between V and Vr is large when Xr is small. FIG. 19 also shows the minute slippage velocity Vr. It can be pointed out that the V and Vr velocity data, although not clearly shown in φ and X data shown in FIGS. 19 and 20 but when observed in detail, sharply increase at φ=0.55 and X=180 µm. We will discuss again whether or not this φ point can be considered as a point where the coefficient of static friction µ is 0.55, including intensity histograms and PIV processing results, which will be described later.

Figure 21:
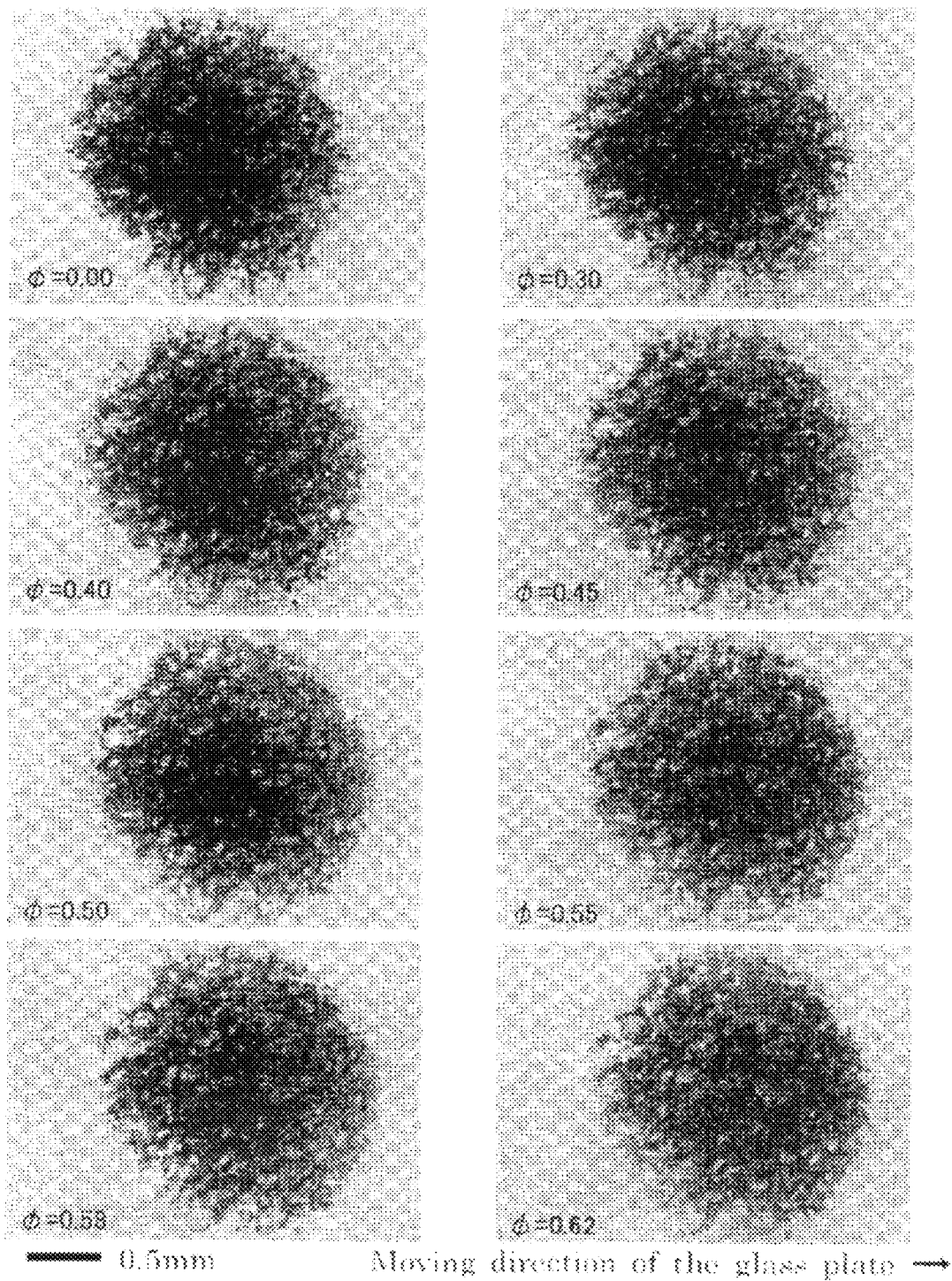
FIG. 21 shows interference images of a real contact area.

FIG. 21 shows representative interference images of a real contact area based on G (green) pixels, which are used in intensity analysis. FIG. 21 clearly shows that the meshed black portion becomes slightly sparser as φ increases and that the real contact area changes accordingly.

In the following, a description of statistic analysis of intensity data in the slippage initiation process will be given.

In this analysis, G-pixel interference fringe intensity data having undergone the background correction are used. The data are obtained by acquiring a reference image with no interference fringe and subtracting the reference image from the G-pixel interference fringe image to correct the background so that unevenness in illumination luminance does not affect the image analysis. G pixels are used in consideration of the balance between the sensitivity and the resolution (shorter wavelength provides higher resolution). The image analysis has been reported and basic data are acquired in the steps of image acquisition, RGB separation, background correction on G pixels, intensity data acquisition, and intensity histogram creation [1].

Figure 22:
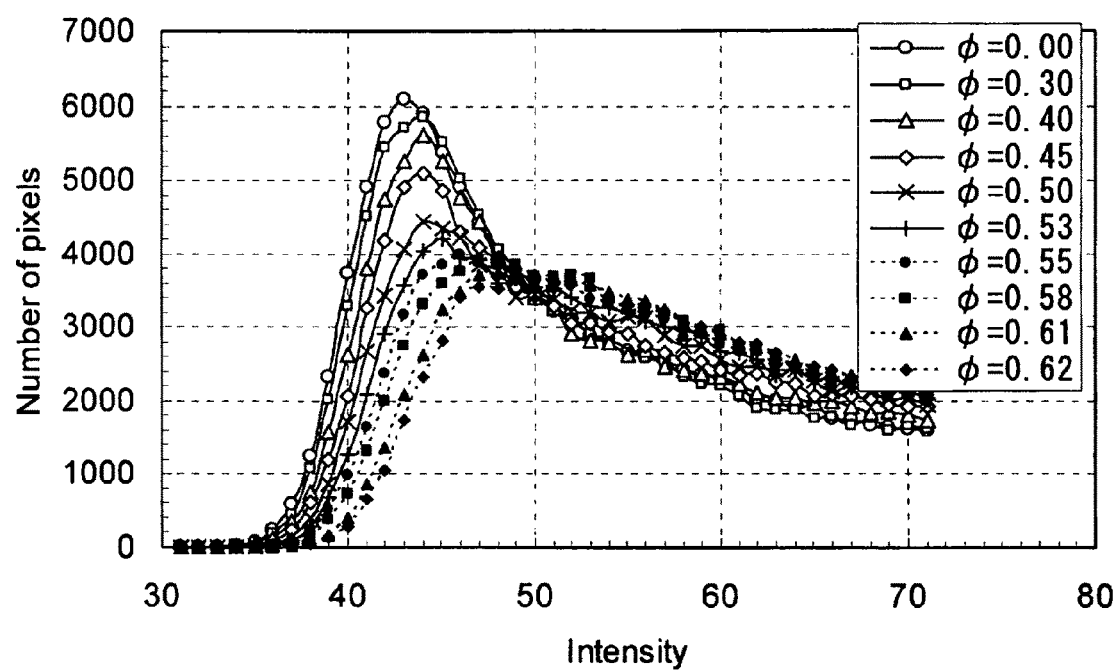
FIG. 22 shows intensity histograms for a variety of tangential force coefficients φ(W=2.5 N)

Next, intensity histograms will be described. FIG. 22 shows intensity histograms that represent the slippage initiation process and are obtained for 10 different levels of tangential force coefficient $\phi$. Each of the intensity histograms only includes an enlarged low-intensity distribution relating to information on a real contact area. As shown in this figure, each of the distributions, in general, has a peak within a range of the intensity from 43 to 47, and the count (the number of pixels) sharply decreases to zero on the left-end, low-intensity side of the distribution. This portion of the distribution corresponds to the region I, which reflects a real contact area, as described in reference[1]. On the other hand, the right-end distribution tends to converge to a fixed count, which also reflects the fact that there are an infinite number of regions II, each of which has a clearance of several tens of nanometers, in a macroscopically contact region on a rough surface.

The behavior of the count and the intensity in a peak position as the tangential force coefficient $\phi$ increases will next be discussed. The count greatly decreases as $\phi$ increases from 0 to 0.50 but does not greatly change in the range of $\phi$ between 0.55 and 0.62. Accordingly, the intensity ranges from 43 to 44 when $\phi$ ranges from 0 to 0.5, whereas the intensity is higher and ranges from 46 to 47 when $\phi$ ranges from 0.55 to 0.62, that is, the intensity increases by 2 to 3 units on the side where the clearance between the contact surfaces increases. The change described above causes the shape of the peak to change from a steep one to a gentle one as the count in the peak position decreases and the peak position is shifted toward a higher intensity position. The change in any of the intensity histograms that occurs when a tangential force is applied conceivably results from the change in the contact state (clearance) of the real contact area where a stick region and a slip region coexist.

In what follows, normal distribution fitting and a real contact area will be described. Further, statistic analysis of a contact state in the slippage initiation process will be discussed. In the distribution on the low-intensity side of a peak, it is expected that the region I forms a normal distribution shape, which is exactly the same real contact area as described in reference [1]. It is believed that the region I changes its shape while maintaining a normal probability distribution P(I) expressed by the following equation (1) when the tangential force changes:

$$P(I) = \frac{1}{\sqrt{2\pi}\,\sigma} \exp\left\{\frac{-(I - I_m)^2}{2\sigma^2}\right\} \quad (1)$$

Figure 23:
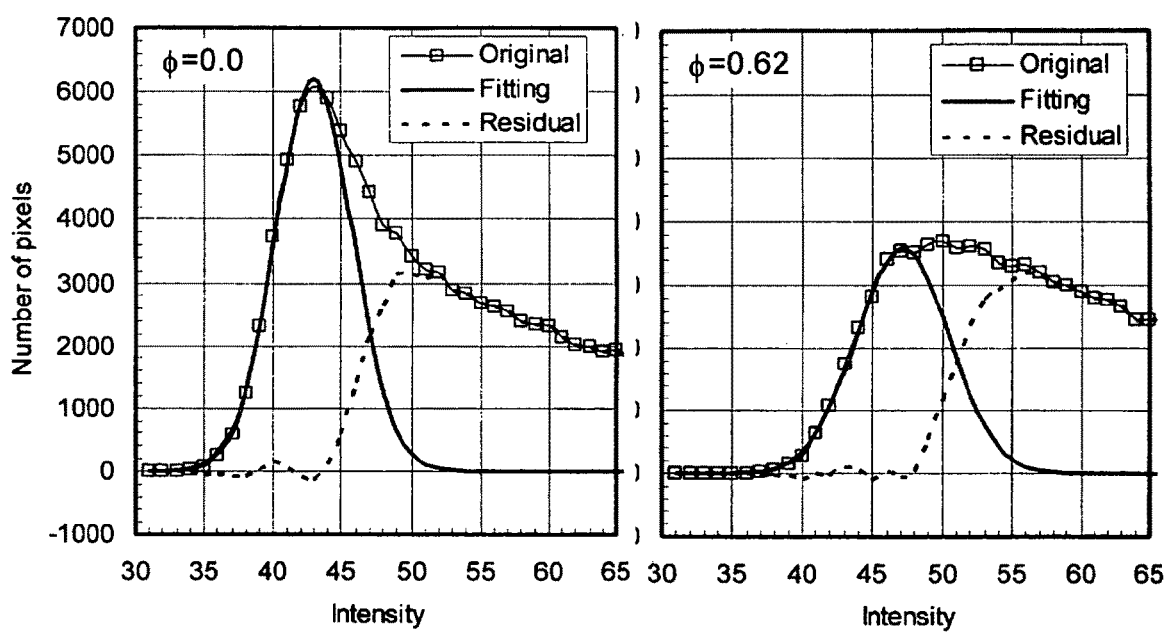
FIG. 23 shows Intensity distribution as a function of number of pixels for both stick and slip regions.

In this Equation, I, $I_m$, and $\sigma$ represent, respectively, the intensity, the mean intensity value, and the standard deviation. Consider now intensity histograms for tangential force coefficients $\phi$ of 0 and 0.62, which correspond to 100% "stick region" and 100% "slip region," respectively. FIG. 23 shows Intensity distribution as a function of number of pixels for both stick and slip regions. As shown in this figure, the distribution of each of the histograms can be divided into two regions; 1) the region I, which follows a normal distribution, and 2) a residual region. As presented in reference [1], fitting is performed on the histogram in question by using an optimization method (using the graph analysis software Origin8 and the Marquardt method). The solid line along the markers on the low-intensity side represents the result of the optimized normal distribution fitting, while the broken line along the markers on the high-intensity side represents the residual region. Further, FIG. 23 shows that the distribution on the left side of the peak fits well with the normal distribution while the residual on the same side maintains the same shape for any value $\phi$.

Figure 24:
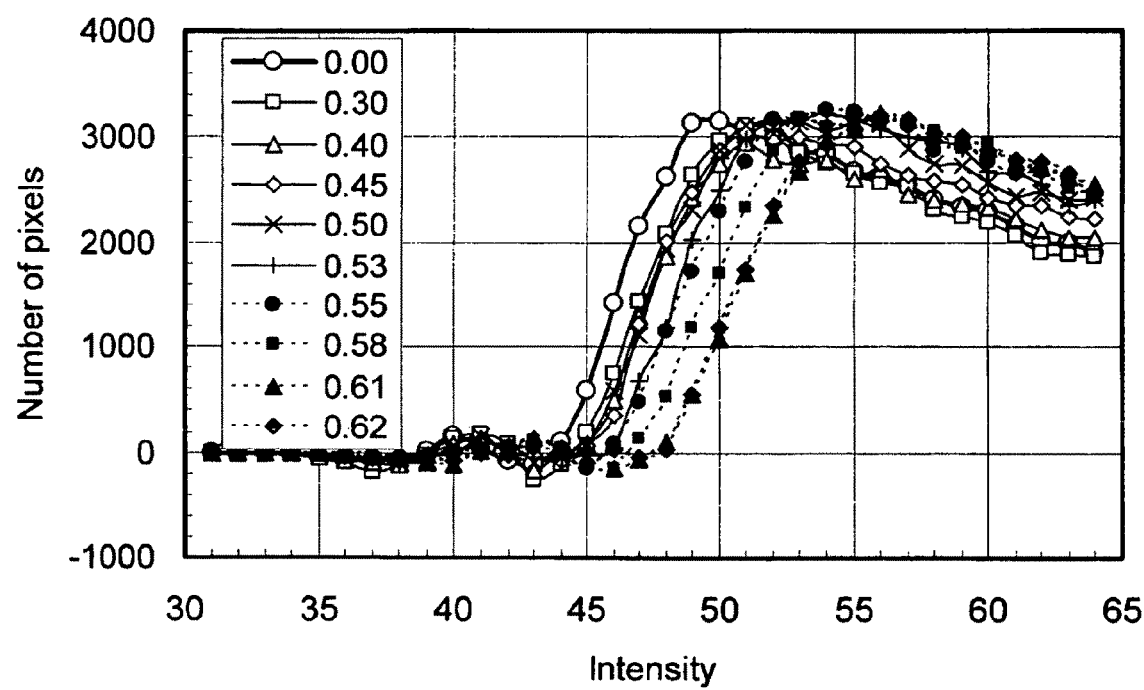
FIG. 24 shows residual histograms as a function of tangential force coefficients (φ)

FIG. 24 shows a histogram of the residual regions calculated for each of the $\phi$ values. As shown in this figure, the residual region has a distribution that includes regions II, which correspond to non-contact areas in the vicinity of the real contact area [1]. The maximum count (the maximum number of pixels) and the shape of any of the residual histograms are substantially the same as those of the others, and the entire shape is shifted to the right as $\phi$ increases. The behavior described above shows that the fitting has been performed in a satisfactory manner and statistic analysis of the contact surface will be made successfully based on the intensity information.

Figure 25:
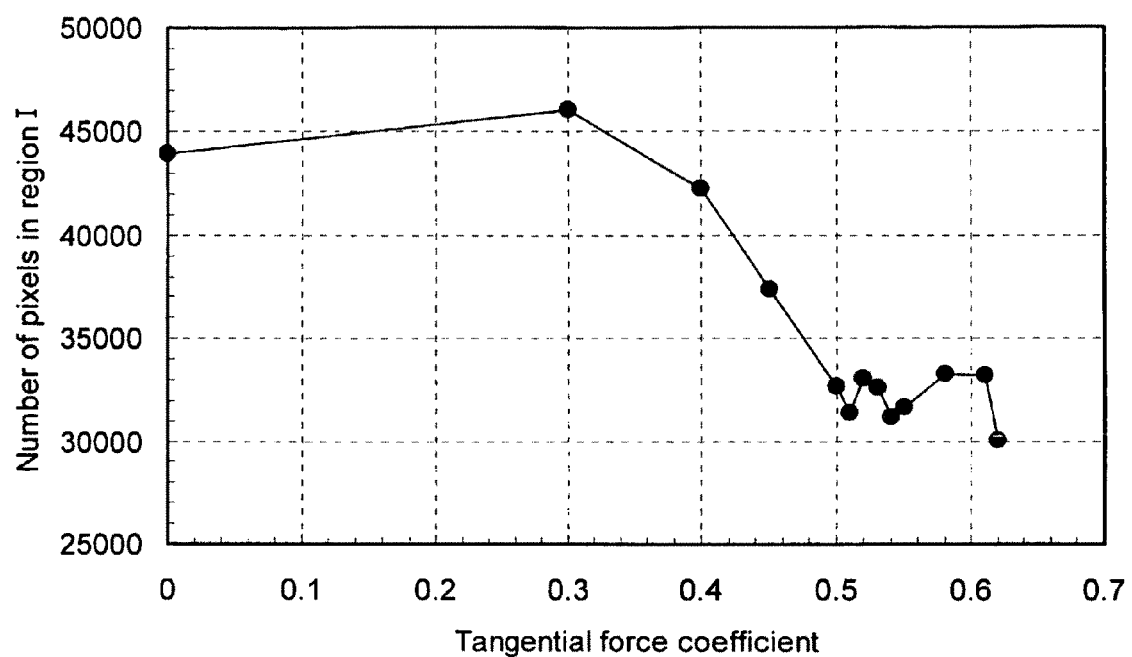
FIG. 25 shows cumulative count in a normal distribution having undergone fitting.
Figure 26:
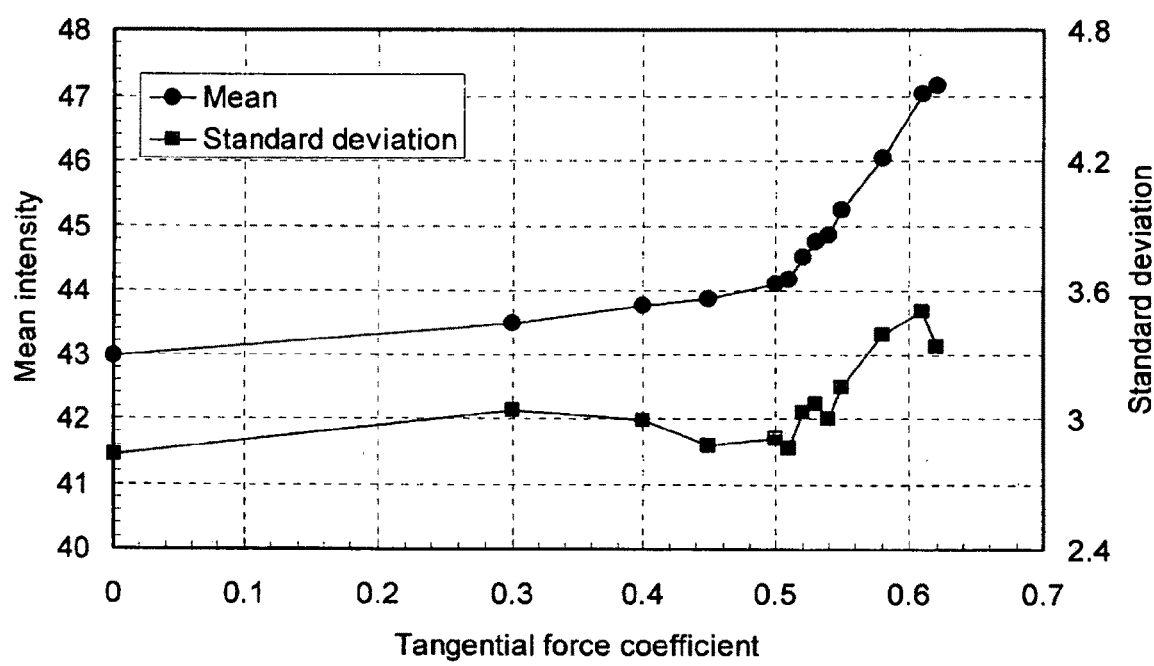
FIG. 26 shows normal distribution parameters of a normal distribution having undergone fitting.

FIGS. 25 and 26 show change in cumulative count and normal distribution parameters (mean intensity Im and standard deviation $\sigma$) of a normal distribution (region I) having undergone the fitting as the slippage initiation process proceeds. As shown in FIG. 25, the count in the region I slightly increases or stays horizontal in the range of $\phi$ from 0 to 0.3 and then monotonously decreases until $\phi$ reaches 0.5. Thereafter, the count stays substantially constant, although unstable and oscillatory. It is conceivable that the count eventually converge although it increases or decreases to some extent. In fact, the application of the tangential force $\phi$ causes the count in the region I to temporarily start decreasing. However, the count stops decreasing at a point beyond $\phi$=0.51 and changes its behavior, which implies that the state enters a transition process to macroscopic slippage.

As shown in FIG. 26, the mean intensity Im increases first gradually and then sharply at $\phi$=0.51, the same point where the count in the region I changes, and keeps increasing afterward. The standard deviation $\sigma$, which has been substantially constant, sharply increases at $\phi$=0.51, temporarily decreases to a local minimum at $\phi$=0.54, and then increases again. The velocity V in the slippage initiation process, shown as described above in FIGS. 19 and 20, increased from $\phi$=0.55, the point of inflection. This increase is small enough to not change clearly the measured tangential force coefficient $\phi$ and the displacement X. But the results of the statistic analysis of the contact interface, shown in FIGS. 19 and 20, show the clear changes as described above. That is, $\phi$ and $\mu$ can be considered to be 0.55.

Figure 27:
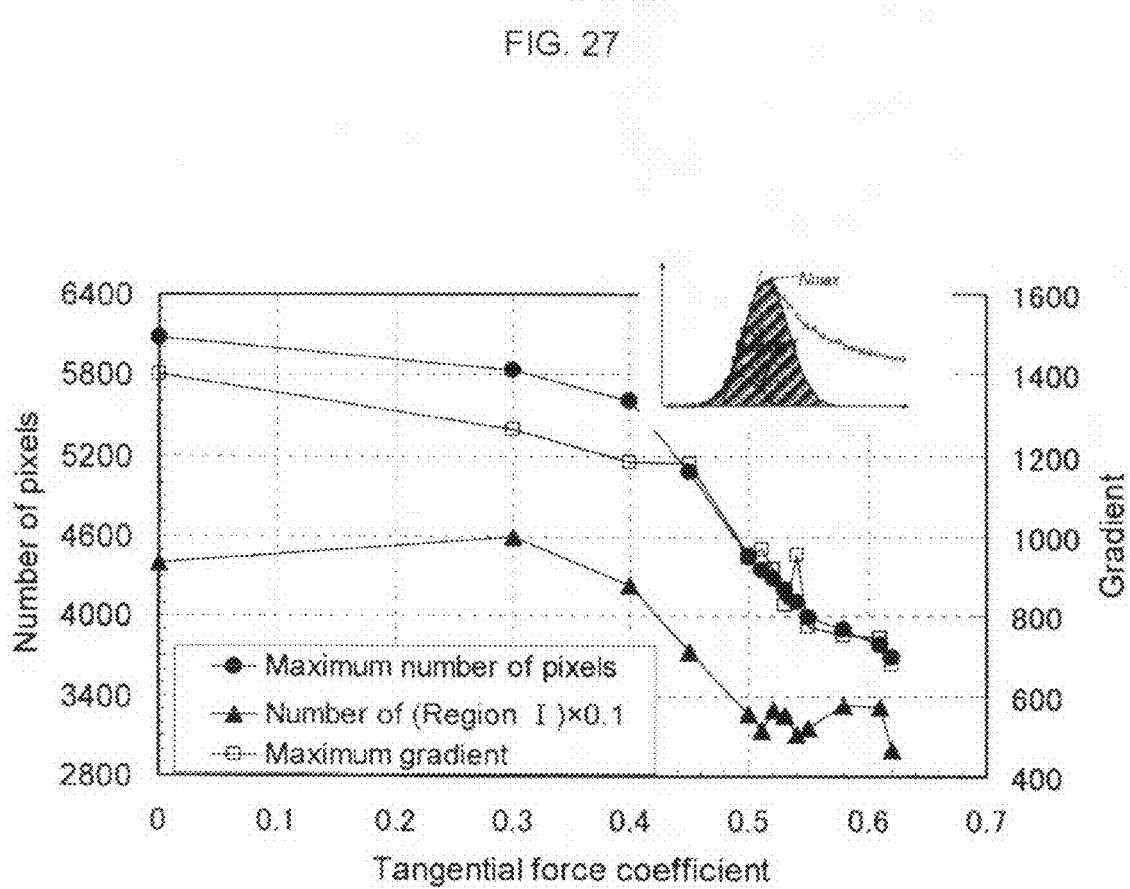
FIG. 27 shows the maximum gradient, the maximum count, and other parameters of a histogram.

Next, the real contact area and characteristic values of the intensity histogram will be described. The characteristics of the change in an intensity histogram in the course of the slippage initiation process also appear in the change in the largest gradient (change in the count per intensity) and the largest count (the number of pixels) of the histogram. FIG. 27 shows the change in the maximum gradient and the maximum count as well as change in the cumulative count in the region I. These three characteristic values monotonously decrease in the range of tangential force coefficient $\phi$ from 0.3 to 0.5. Thereafter, (1) the gradient decreases while showing oscillatory behavior but stops decreasing at $\phi$=0.55, and (2) the maximum count keeps decreasing beyond φ=0.55 but gently decreases when reaching a point of inflection at φ=0.55. The changes in the gradient and the maximum count have substantially the same tendency and are also related to the tendency of the change in the cumulative count.

Figure 28:
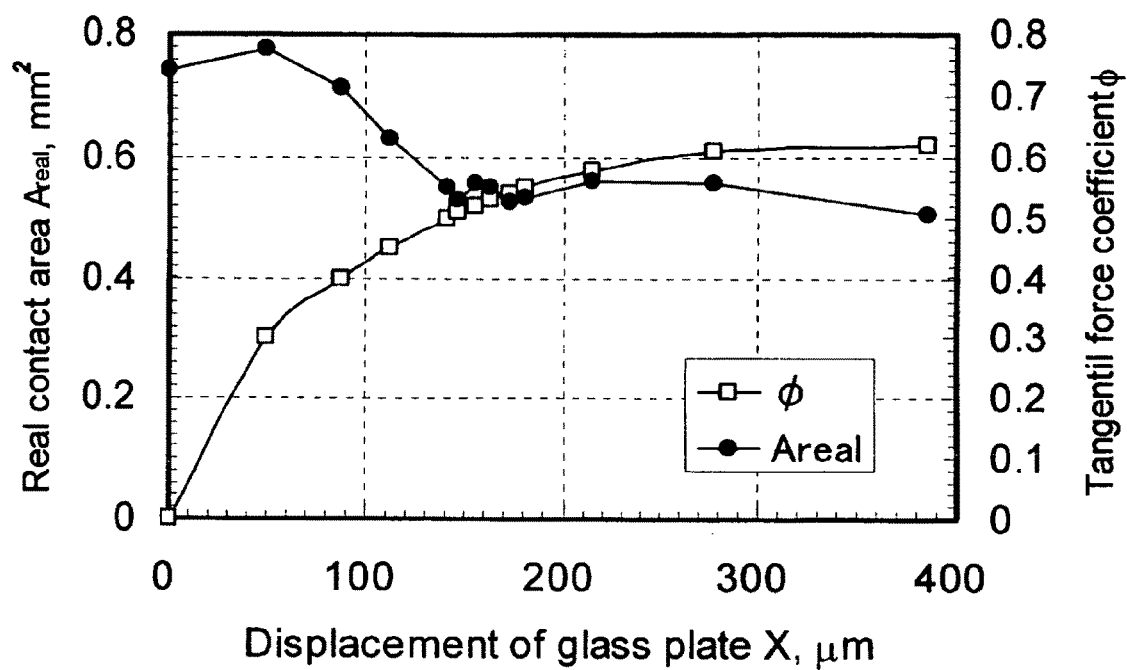
FIG. 28 shows how the real area of contact and the tangential force coefficient change when the displacement increases.

In the following, a description of the real contact area and the real shear stress acting on the interface will be given. FIG. 28 shows how the real contact area $A_{real}$, changes when the displacement X increases in the slippage initiation process. The real contact area $A_{real}$ is calculated from the cumulative count in the region I as described above. In the transition process from the stationary state to a dynamic friction state, the real contact area $A_{real}$ first decreases, then it transitions to a macroscopic slippage state when the real contact area $A_{real}$ reaches a certain value. Afterward, the change in the real contact area $A_{real}$ is small.

Figure 29:
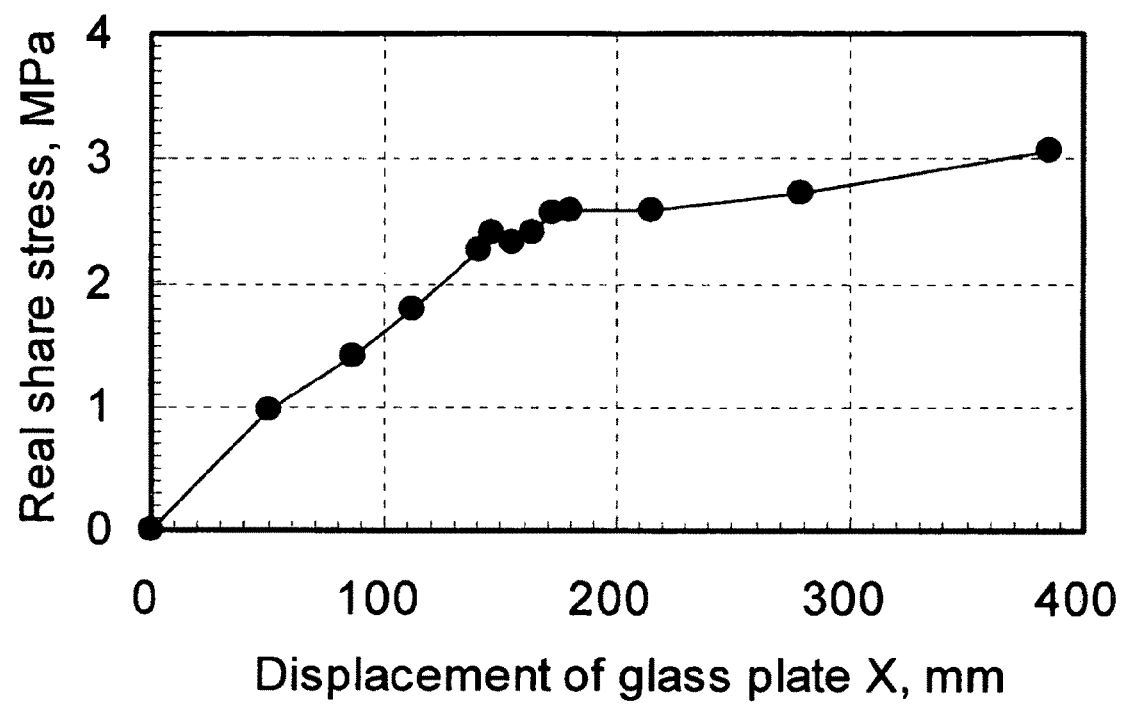
FIG. 29 shows real mean shear stress along a contact interface.

One way to understand the slippage initiation process is to find out the real mean shear stress acting on the contact interface. FIG. 29 shows calculated real mean shear stress at the interface by using the following equation (2):

$$\text{Real mean shear stress} = \frac{\text{Tangential force}}{\text{Real contact area}} \quad (2)$$

In FIG. 29, the horizontal axis represents the displacement X of the glass plate, and the vertical axis represents the calculated real mean shear stress. FIG. 29 shows that the shear stress increases substantially linearly in a first section up to a displacement of 150 μm. The shear stress stays substantially constant in the following section to a displacement of 220 μm (φ=0.5 to 0.58), and then further increases. FIG. 29 can also be interpreted as a basic diagram of a tribology phenomenon that is equivalent to a stress-strain diagram in a material test (In the present experiment, although the shear strain is not measured, it can be approximately calculated by considering the surface roughness). In this way, the friction transition from static friction to dynamic friction is interpreted as a consistent interface shear breakage process [6].

In what follows, a description of visualization based on PIV analysis will be given. Since part of the dark portion of an acquired interference image also reflects a non-contact area having a tiny clearance, only a real contact area is not visualized in an exact sense. To address the problem, the present inventor has considered that using the same data (interference image) described above to perform analysis based on PIV (particle image velocimetry) using a real contact point as a tracking marker may judge whether a portion in question is a real contact area and the point is stuck or slipping.

Next, the method for performing the analysis and results thereof will be described. Dedicated software FlowPIV is used in the analysis. Although the software is inherently used to measure a flow vector by using information on intensity (particle position) of an image, the software can be used in the invention because a real contact point can be considered as a particle and the movement of the particle (based on sticking or slipping) is tracked [3, 4]. The setting used in this analysis is shown in Table 1:

TABLE 1

Setting in PIV processing

| | |
|---|---|
| Interval of measurement frame | 10 frames (0.33 second) |
| Interval of grid | X: 6, Y: 6 |
| Tracking size | 9 |
| Base size | 23 |

The setting of the PIV processing, in the present example, will be described as follows. The PIV processing is performed on an interference image and an image frames 10 thereafter (after 0.33 second) for each value φ. The result of the PIV processing is outputted in the form of a velocity vector, where the length and the frequency thereof can be obtained. Horizontal and vertical intervals between points of a grid based on which the vector is measured are set. Further, a tracking size in which a moved measurement point is searched is specified by the number of pixels. All points around each measurement point in the tracking size are searched. Further, a base size used to compare density unevenness patterns is specified by the number of pixels. Images around each measurement point within this size are compared for the tracking.

Consider now a case where the present test apparatus is used to view a contact surface under friction. It is assumed that a stick region and a slip region are created in the portion where a spherical test piece comes into contact with a glass plate when a tangential force φ is applied. When the contact surface is viewed under a microscope, the stick region is pulled by the glass plate and moved accordingly because the stick region is in intimate contact with the glass plate. On the other hand, the slip region stays there and does not move because the slip region and the glass plate are under dynamic friction. When the PIV analysis is carried out by using the present test apparatus, a vector according to the velocity of the glass plate is formed in the stick region, whereas no vector is formed in the slip region.

Figure 30:
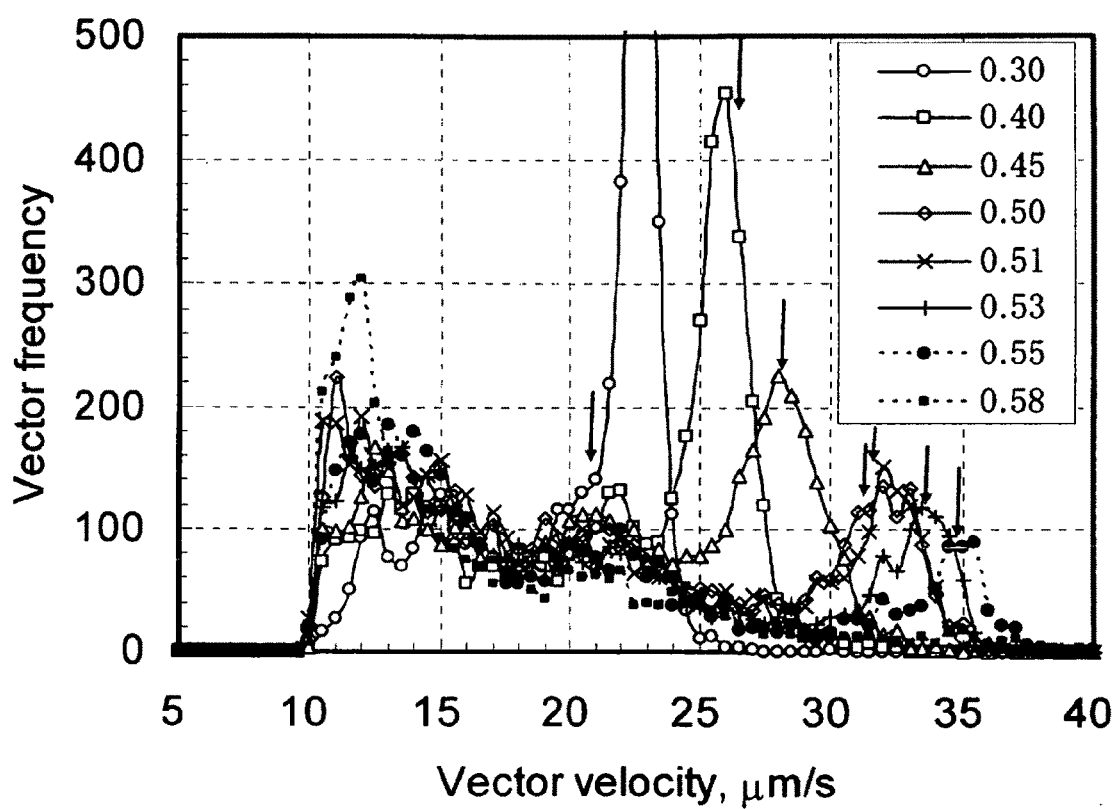
FIG. 30 shows results of PIV analysis.

FIG. 30 shows histograms of the velocity vector of a tracking marker determined by the PIV analysis with the horizontal axis representing the vector velocity and the vertical axis representing the frequency of occurrence of the velocity vector. As described above, the speed at which the glass plate is driven is not constant in the present experiment. Since the velocity vector formed in the stick region has the same speed as the speed at which the glass plate is driven, the frequency of occurrence should be maximized at this speed. In fact, the measured speed at a peak point in the velocity histogram for each value φ is equal to the speed at which the glass plate is driven (arrow), as shown in FIGS. 19 and 20, within an accuracy of ±0.5 μm/s, and the vector frequency decreases while the peak point is shifted to the right as the value φ increases. The reason why the peak vanishes at φ=0.58 is that the stick region vanishes because the state changes to the macroscopic slippage state. Further, the reason why the frequency of the velocity vector is broadly distributed will be discussed below.

A description of identification of the stick region is as follows. In FIG. 30, the distribution having a peak point and located in the vicinity of the driving speed is obtained by calculating the velocity directly from the travel of the tracking point that remains in the stick state. In the present example, since the value φ is defined at a lower speed at which the glass plate is driven, the measured vector velocity is greater than the speed V of the glass plate by approximately 1 μm/s at the maximum. Further, measurement variation is conceivably added to the measured vector velocity.

In the distribution on the low-speed side of the peak point, slippage occurs at the real contact point, which is the tracking point, at a certain probability. When the state at the tracking point changes from the stick state to the slip state, the travel of the tracking point decreases due to the slippage. The vector velocity at the tracking point is calculated based on the thus decreased travel, but the tracking point is in the stick state at the start point where the value φ is defined. The inventor therefore assumes that the lower-limit vector velocity, by which the measured velocity vector is judged to be in the stick state, is set to the minute slippage velocity Vr, which statistically reflects the above-mentioned description.

Figure 31:
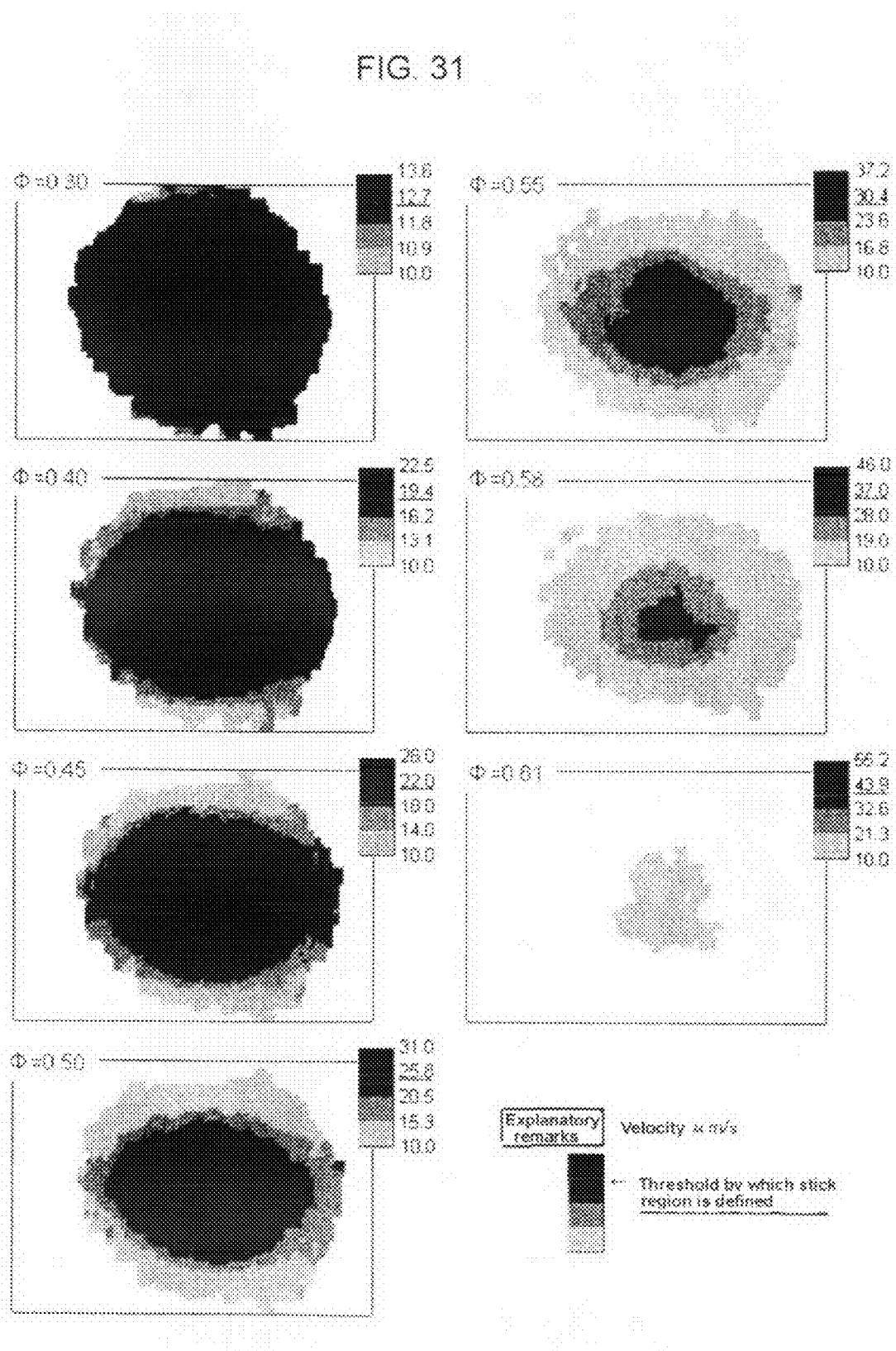
FIG. 31 shows mapped velocity vectors obtained by the PIV processing.

FIG. 31 shows velocity vectors obtained by the PIV processing and mapped in grayscale. Each display bar is divided into four grayscales for clarity with a darker scale representing a higher velocity and a lighter scale representing a lower velocity. As indicated by the explanatory remarks, the darkest grayscale portion in any of the sections in FIG. 31 represents a region where the vector velocity is at least minute slippage velocity Vr for the value φ (slightly lower than the speed V at which the glass plate is driven as described above and corresponding to the threshold that defines the stick region), that is, the stick region. The other regions can be estimated to be the slip region. The present apparatus thus successively reproduced and visualized an annular slip [3] state in which the stick region and the slip region coexist.

Figure 32:
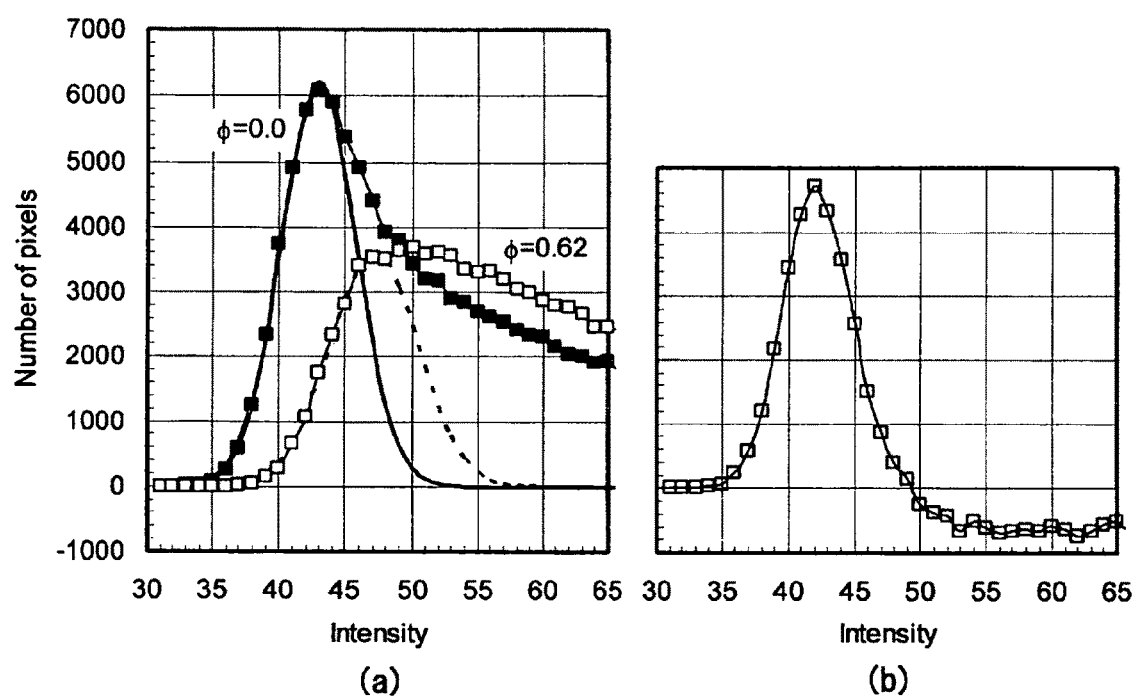
FIG. 32(a) shows intensity histograms.
FIG. 32(b) shows an intensity difference histogram.

Next, statistic analysis of the "stick region" will be described. Local stick regions can be mapped by using PIV. It is therefore possible to study general transition of the proportion of the stick region. In the present example, however, a simper method for statistically calculating the proportion of the stick region will be discussed In the following, an intensity difference histogram will be described. The present inventor considers that in the slippage initiation process, the change in real contact area intensity can be statistically obtained by subtracting a histogram with the tangential force coefficient φ=0 as a reference from a histogram with an arbitrary φ. The calculation of the intensity difference histogram will be described in FIG. 32 with reference to a case where the state is definitely the macroscopic slip state, φ=0.62. A zero-cross point (intensity of 49) that intersects the horizontal axis, where the difference in count (the number of pixels) is zero, clearly divides the intensity difference histogram into a positive region, approximated to a normal distribution having its center at intensity of 42, and a negative region, which is located on the side where the intensity is higher than 49 and where the count gently approaches a fixed value. The positive region of the difference histogram stands for a decrease in the number of pixels in the stick region as the tangential force increases, and the absolute value of the negative region stands for an increase in the number of pixels in the slip region.

Figure 33:
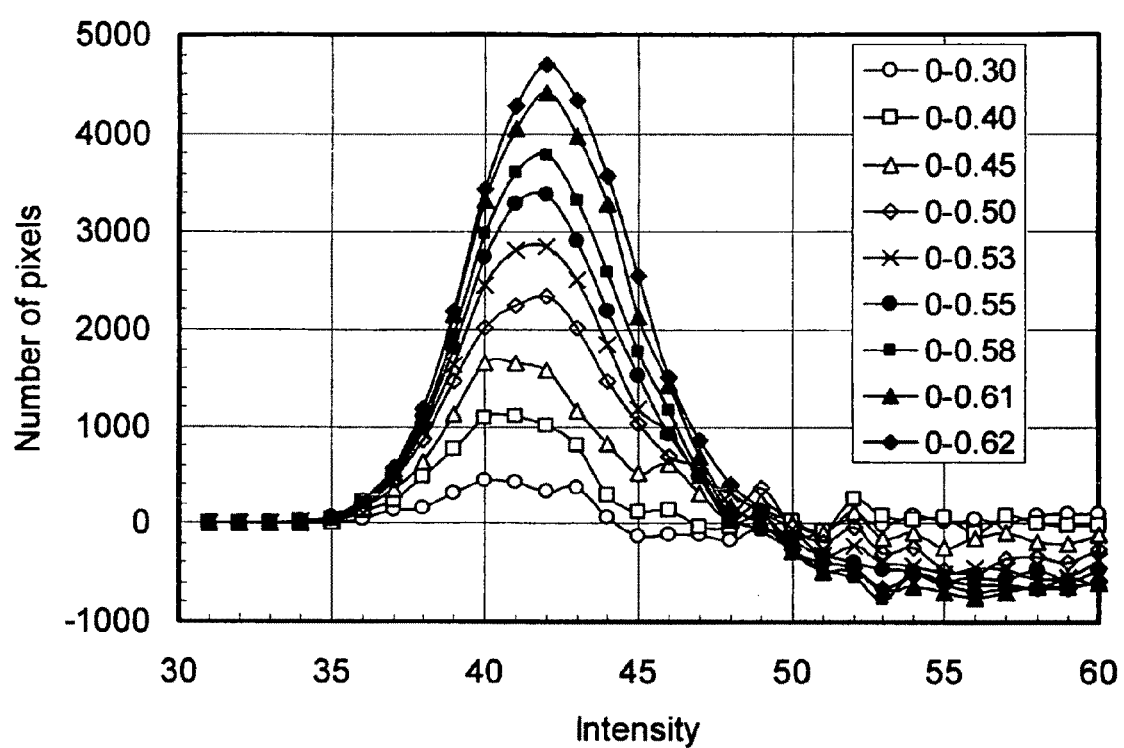
FIG. 33 shows intensity difference histograms for a variety of tangential force coefficients.

FIG. 33 shows difference histograms for representative tangential force coefficients in the slippage initiation process. Within the range of φ from 0.55 to 0.62, which is believed to correspond to a state after macroscopic slippage is initiated, each distribution in the positive region has strong similarity to a normal distribution having its center at the intensity of 42. On the other hand, within the range of φ from 0.3 to 0.5, which corresponds to a state before macroscopic slippage is initiated, each distribution has weak similarity to the normal distribution having its center at the intensity of 42. In addition, the intensity at the zero-cross point is shifted to the left of the intensity of 49. As described above, the size of the positive region of the difference histogram increases as the slippage initiation process proceeds, and the mean value point of the region also moves. The similarity to the normal distribution conceivably correlates with the change in contact state, whether two surfaces in contact with each other are under static friction or dynamic friction.

Figure 34:
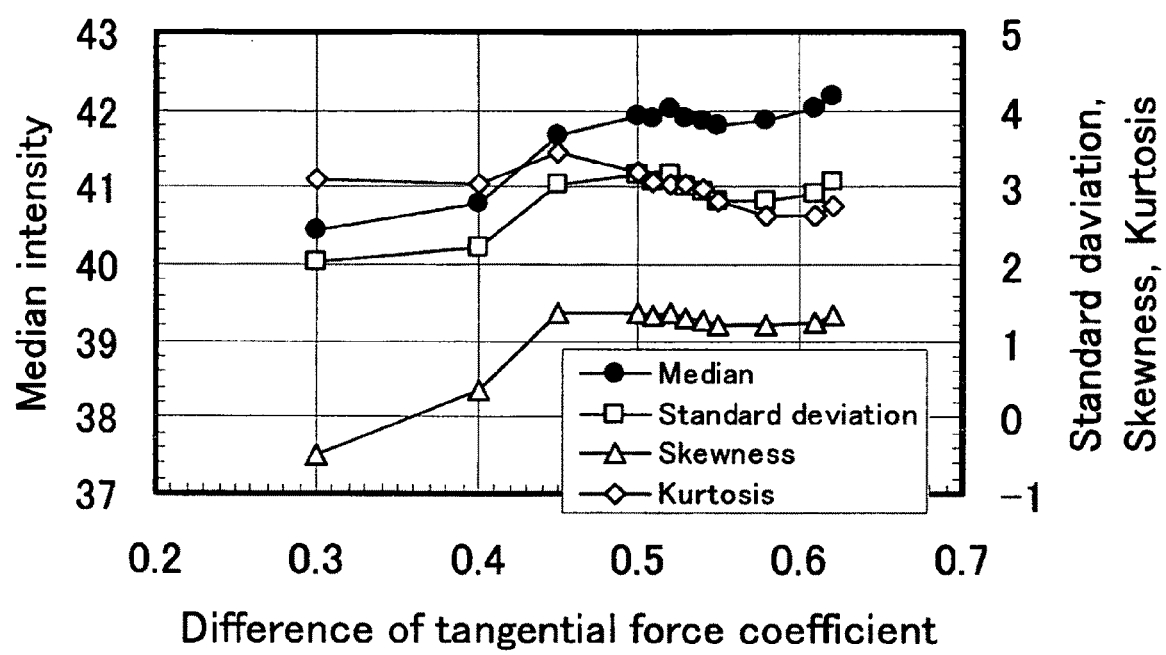
FIG. 34 shows statistic characteristics of a normal distribution.

To investigate the correlation, the following values showing statistic characteristics of the distribution of the positive region are determined: (1) mean intensity (Im), (2) standard deviation (σ), (3) skewness (s), and (4) kurtosis (k). FIG. 34 shows the measured statistic characteristics of the normal distribution. When the distribution is similar to a normal distribution, it is expected that the mean intensity (Im) to be a median of the distribution in consideration of its symmetric shape. Also, it is expected that the skewness (s) be zero, and the kurtosis (k) be 3. The skewness (s) is conceivably slightly positive because there is a negative region resulting from a distribution calculating method which will be discussed in this section. The tendencies in the mean intensity (Im), the standard deviation (σ), and the skewness (s) are substantially the same and have local minimums at φ=0.55. The correlation between the similarity to the normal distribution and the initiation of macroscopic slippage can be adequately pointed out based on the standard deviation by way of example. The kurtosis (k) does not have a local minimum at φ=0.55 but has a local minimum, which is slightly smaller than 3, in the range of φ from 0.58 to 0.61. The reason for this is related to the above-mentioned distribution calculating method.

Figure 35:
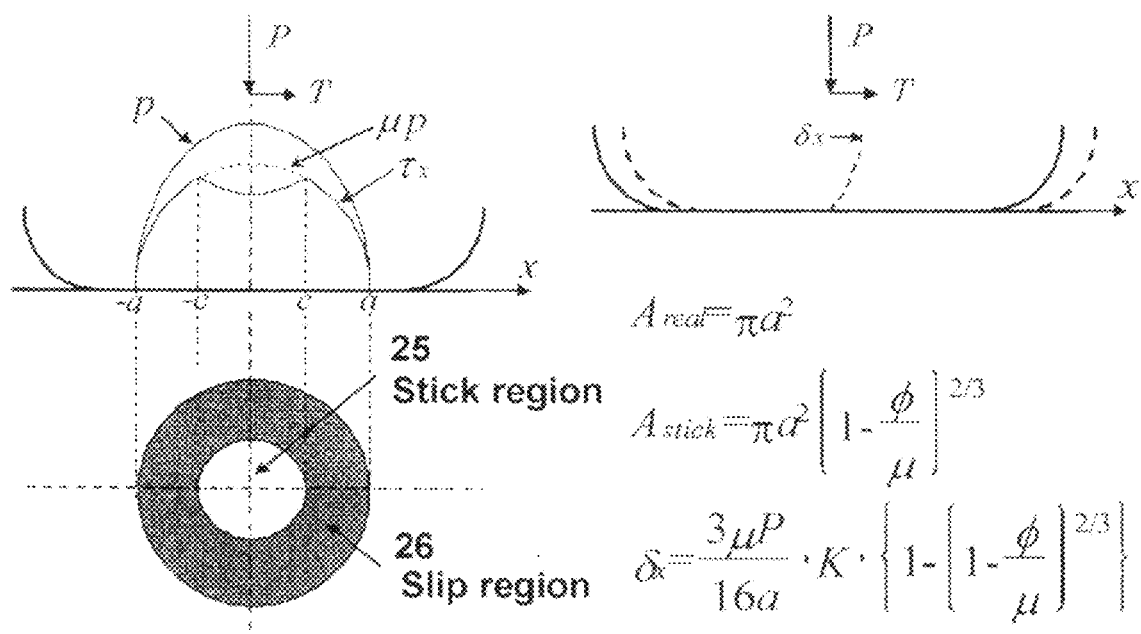
FIG. 35 shows a theoretical relationship in the Hertzian contact on a smooth surface.

The proportion of the stick region will be described as follows. The proportion of the "stick region" in the real contact area changes from 1 to 0 when the stationary state transitions to the dynamic friction state in the slippage initiation process. A minute slippage occurrence region where the "stick region" and the "slip region" coexist is an intermediate region between the two states. FIG. 35 shows a theoretical relationship in the Hertzian contact on a smooth surface [3]. In FIG. 35, P represents the normal force, T represents the tangential force, p represents the Hertzian contact pressure distribution, and K represents a constant determined by the material of the test piece and other factors.

Next, change in the contact state of the above-mentioned real contact area will be discussed based on the analysis results shown in FIG. 36. The horizontal axis represents the ratio of the tangential force coefficient φ to the coefficient of static friction μ, and the vertical axis represents the proportion of the stick region, which will be defined below.

The first way to calculate the "proportion of the stick region," or "stick region proportion 1" is to use a difference histogram by the following equation (3):

$$\text{Stick region proportion 1} = \tag{3}$$
$$1 - \frac{\text{The number of pixels in positive region for } \phi}{\text{The number of pixels in positive region for } \mu}$$

The number of pixels in the positive region of the difference histogram is a decrease in the number of pixels in the stick region for the tangential force coefficient φ from the number of pixels in the stick region for φ=0. The decrease ratio of the number of pixels in the stick region for φ is determined by calculating the ratio of the decrease in the number of pixels in the stick region for φ to an eventual decrease in the number of pixels in the stick region for the coefficient of static friction μ. Subtracting the decrease ratio described above from one produces the remainder ratio in the stick region. The present inventor considers that macroscopic slippage is initiated at μ=0.55 and plotted a graph labeled with "Ratio 1" in FIG. 36. In this case, since all the real contact area for μ=0.55 is a slip region, the number of pixels in the positive region of the difference histogram at this point should be equal to the number of pixels in the region I (corresponding to the real contact area). In practice, however, the ratio between them (the number of pixel in the positive region for μ=0.55/ the number of pixels in the region I for μ=0.55) is 21200/ 31700=0.669, which is not 1. On the other hand, when μ is 0.62, the ratio is 30100/30000=1.00, which is equal to 1. The second way to calculate the "proportion of the stick region,"

or "stick region proportion 2" is to use the following equation (4):

$$\text{Stick region proportion 2} = 1 - \frac{\text{The number of pixels in positive region for } \phi}{\text{The number of pixels in region } I \text{ for } \phi} \quad (4)$$

By comparing the results obtained from "the stick region proportion 1" and "the stick region proportion 2", it is observed that the change in the proportion 1 overlaps with the change in the proportion 2 except in the range where the proportion 2, $\phi/\mu$, is approximately 0.58/0.62=0.94 or higher. It is therefore demonstrated that general characteristics of the slippage initiation process can be expressed by the proportion 1, which can be readily calculated only by a difference histogram.

The third way to calculate the "stick region proportion," or "stick region proportion PIV" ($\mu$=0.55) is to use the PIV analysis by the following equation (5):

$$\text{Stick region proportion } PIV = \frac{\text{The sum of the number of vectors having velocity } V_r \text{ or higher}}{\text{The total number of measured velocity vectors}} \quad (5)$$

The equation (5) is obtained by using the velocity Vr for each $\phi$ value as a threshold in the histograms of the measured velocity vectors shown in FIG. 30. Further, the equation (5) is obtained by assuming that the sum of the number of vectors whose velocity is higher than the velocity Vr correspond to the stick region. The above-mentioned stick region proportions, "stick region proportion 1," "stick region proportion 2," and "stick region proportion PIV," substantially coincide with one another across the range indicated by the data except the slight remainder of the sum of the number of vectors in the vicinity of $\phi/\mu$=1.

Figure 36:
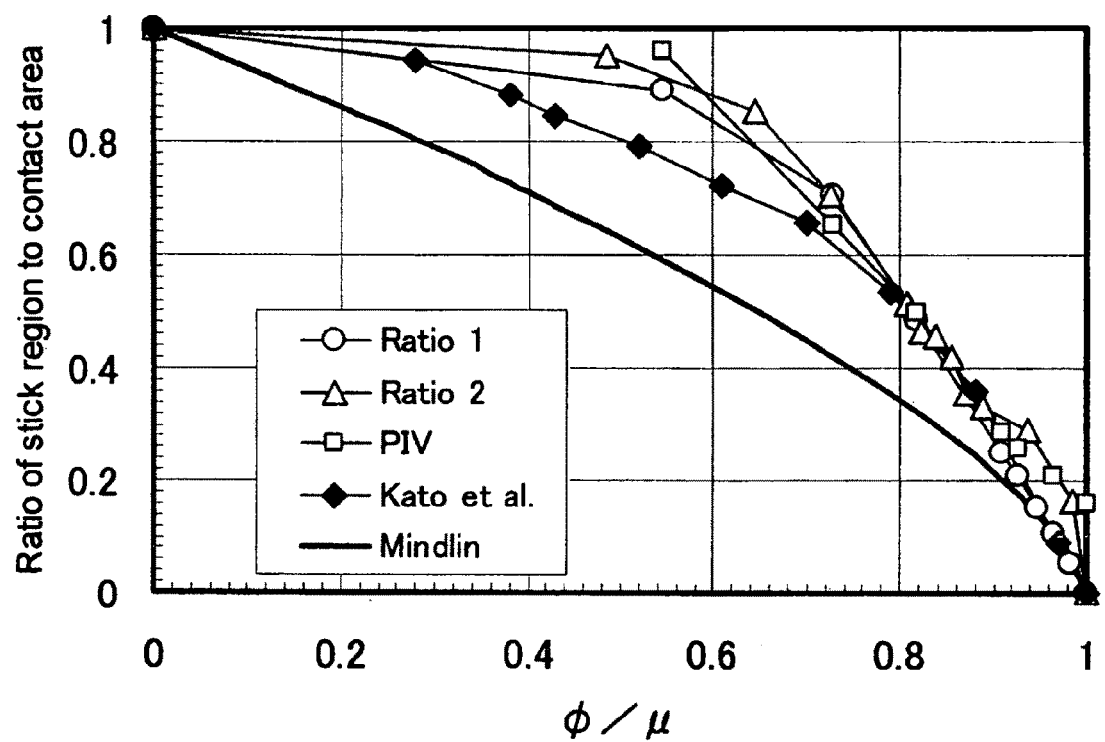
FIG. 36 shows change in contact state of a real contact area.

FIG. 36 further illustrates experimental results obtained by Kato et al. [2] and theoretical values derived by Mindlin [3]. The former experimental results uses a correlation method in which a smooth rubber surface is the object of interest. The present experimental results show that the results derived by Kato et al. are greater than the PIV results when $\phi/\mu$ is small and greater than the theoretical values derived by Mindlin across the entire range. The reason for occurring the above-mentioned discrepancy will be discussed further below.

Figure 37:
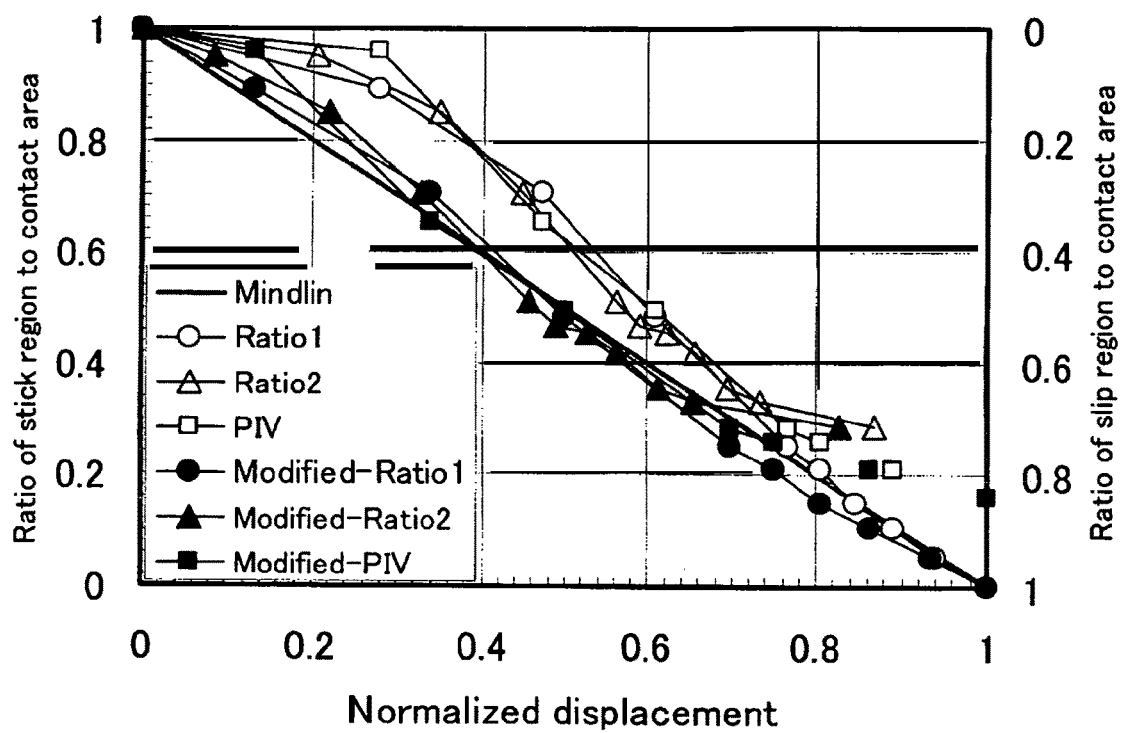
FIG. 37 shows graphs of the proportion of the stick region versus a normalized displacement.

In the following, the stick region proportion and minute slippage displacement will be described. FIG. 37 shows graphs of the stick region proportion versus a normalized displacement X/Xslip (Xslip: displacement for $\mu$) in the slippage initiation process. The theoretical values derived by Mindlin [3] are expressed by a straight line having a gradient of −1. The graph labeled with "Ratio 1" represents the results of the above-mentioned "stick region proportion 1" versus the displacement X without correction. On the other hand, the graph labeled with "Modified-Ratio 1" represents the same "stick region proportion 1" but versus the minute slippage displacement Xr, which is obtained by subtracting the value corresponding to the elastic deformation line, shown in FIG. 20, from the displacement X without correction.

As shown in FIG. 37, the values on the low $\phi/\mu$ side (low normalized displacement) have been corrected, and the corrected values linearly decrease in accordance with the theoretical values derived by Mindlin. Similarly, the graphs labeled with "Ratio 2" and "PIV" represent the "stick region proportion 2" and the "stick region proportion PIV" versus the displacement X without correction. The graphs labeled with "Modified-Ratio 2" and "Modified-PIV" represent "Ratio 2" and "PIV" having undergone the above-mentioned correction. In this case as well, the values on the low $\phi/\mu$ side have been corrected and the corrected values substantially linearly decrease in accordance with the theoretical values derived by Mindlin. It is noted that the normalized displacement in "Ratio 2" and the "Modified-Ratio 2" is determined by using Xslip, which is determined based on the point corresponding to $\phi$ (=$\mu$)=0.60. Since a slight difference in $\phi$ causes Xslip to greatly change in a region where macroscopic slippage occurs, X/Xslip is greatly affected. In this example, Xslip for $\phi$=0.60 was optimum.

The behavior in the slippage initiation process shows that the minute slippage displacement Xr along the contact interface is important. The behavior in the slippage initiation process similarly implies that the minute slippage velocity Vr [7] should be used as a velocity threshold to extract the stick region even in the above-mentioned "stick region proportion PIV". The reason why the present experimental results, shown in FIG. 36, are greater than the theoretical values derived by Mindlin is conceivably that the test piece used in the present example involves flat surface-spherical surface contact in which modulus of elasticity differ from each other and the spherical surface is a rubber rough surface. Kato et al. has also discussed that the discrepancy of their experimental results from Mindlin's solution resulted from use of a rubber test piece. The calculation of the "stick region proportion" using the difference histogram is simple because it only depends on the change in the intensity of the contact surface, and the shift of each real contact point is statistically calculated, whereby the measurement is advantageously robust against noise.

In summary, white-light interferometry is used to visualize the portion where a rough-surface rubber hemisphere is in contact with a glass surface under no lubrication, and information on the intensity of the interference image is used to analyze the contact state of the real contact area in the slippage initiation process. The following results have been provided:

(1) The region of the lowest-intensity-side distribution of an interference image intensity histogram undergoes normal distribution fitting, and the extracted region is considered as the real contact area. The area of the real contact area decreases as the loaded tangential force increases and becomes substantially constant when macroscopic slippage occurs.

(2) Characteristic values representing the shape of an intensity histogram and the shape of an extracted normal distribution are related to the transition from the "stationary state" to the "minute slippage occurrence state" and "macroscopic slippage occurrence state."

(3) Real shear stress obtained by dividing the tangential force by the real area of contact linearly increases in the minute slippage occurrence state as the displacement of the glass plate increases and reaches a substantially constant value in the macroscopic slippage occurrence state.

(4) Using intensity difference histograms using $\phi$=0 as a reference allows statistic calculation of the stick region proportion in a real contact area the area of which decreases as the loaded tangential force (minute slippage occurrence) increases.

(5) PIV analysis using a real contact point as a tracking marker is performed to successfully visualize the "stick region/slip region" distribution in a real contact area based on a velocity vector. The resultant stick region proportion substantially coincides with the result obtained by using a difference histogram.

(6) The stick region proportion determined by using a difference histogram linearly decreases from 1 to 0 as the "relative displacement at the contact interface (minute slippage)" increases and tends to coincide with the theoretical solutions derived by Mindlin.

While the principles of the disclosure have been described above in connection with specific apparatuses and methods, it is to be clearly understood that this description is made only by way of example and not as limitation on the scope of the invention.

References

[1] Takashi Shibamiya, Masao Eguchi, and Takashi Yamamoto, "Measurement of real area of contact using intensity of white light interferometry," Japanese Society of Tribologists, Proceedings of Tribology Conference, (May, 2008, Tokyo), page 11.

[2] Liu Jun, Kohtaro Ohba, Koji Kato, and Hikaru Inooka, "Partial slip visualization at contact surface with the correlation method", Journal of the Visualization Society of Japan, 15, 57 (1995), pp. 133-139.

[3] Mindlin, R. D, "Compliance of Elastic Bodies in Contact," J. Applied Mechanics, 16, (1949) page 259-268.

[4] Koji Kato, "Micro-Slip against Rubber in Friction Drives," Tribologists, 42, 5 (1997), pp. 369-374.

[5] Shigeo Minami (editor), "Waveform Data Processing for Scientific Measurement," CQ Publishing Co., Ltd. (1986), page 90-93.

[6] Japanese Society of Tribologists, "Friction/wear tests and their applications," YOKENDO Co., Ltd. (2007), page 120-121.

[7] Japanese Society of Tribologists, "Tribology Handbook," YOKENDO Co., Ltd. (2001), page 13-15.

What is claimed is:

1. A contact area measuring apparatus comprising:
   a light transmissive substrate in contact with a specimen;
   illumination means for illuminating the light transmissive substrate with white light from the opposite side of the light transmissive substrate to the specimen;
   interference image acquisition means for acquiring an interference image produced by the light reflected off the specimen and the light reflected off the light transmissive substrate;
   intensity histogram creation means for creating an intensity histogram from information on the intensity of the interference image; and
   contact area computation means for calculating a contact area from the intensity histogram,
   wherein the contact area computation means separates the intensity histogram into a plurality of normal distributions by using optimized approximation of complex normal distribution and calculates the contact area only from the lowest-intensity normal distribution.

2. The contact area measuring apparatus according to claim 1, wherein the interference image acquisition means acquires an interference image and information on the intensity of the interference image.

3. The contact area measuring apparatus according to claim 1, wherein the intensity histogram creation means forms separate RGB intensity information from the information on the intensity of the interference image and creates a G-intensity histogram.

4. The contact area measuring apparatus according to claim 1, wherein:
   the interference image acquisition means acquires an interference image and information on the intensity of the interference image,
   the intensity histogram creation means forms separate RGB intensity information from the information on the intensity of the interference image and creates a G-intensity histogram, and
   the contact area computation means separates the G-intensity histogram into a plurality of normal distributions by using optimized approximation of complex normal distribution and calculates the contact area only from the lowest-intensity normal distribution.

5. A contact area measuring method comprising the steps of:
   placing a specimen on a light transmissive substrate so that the specimen comes into contact with the light transmissive substrate;
   illuminating the light transmissive substrate with white light from the opposite side of the light transmissive substrate to the specimen;
   acquiring an interference image produced by the light reflected off the specimen and the light reflected off the light transmissive substrate;
   creating an intensity histogram from information on the intensity of the interference image; and
   calculating a contact area from the intensity histogram,
   wherein the intensity histogram is separated into a plurality of normal distributions by using optimized approximation of complex normal distribution and the contact area is calculated only from the lowest-intensity normal distribution in the contact area computation step.

6. The contact area measuring method according to claim 5, wherein an interference image and information on the intensity of the interference image are acquired in the interference image acquisition step.

7. The contact area measuring method according to claim 5, wherein separate RGB intensity information is formed from the information on the intensity of the interference image and a G-intensity histogram is created in the intensity histogram creation step.

8. The contact area measuring method according to claim 5, wherein:
   an interference image and information on the intensity of the interference image are acquired in the interference image acquisition step,
   separate RGB intensity information is formed from the information on the intensity of the interference image and a G-intensity histogram is created in the intensity histogram creation step, and
   the G-intensity histogram is separated into a plurality of normal distributions by using optimized approximation of complex normal distribution and the contact area is calculated only from the lowest-intensity normal distribution in the contact area computation step.

9. A contact area measuring apparatus comprising:
   a light transmissive substrate in contact with a specimen;
   driving means for moving the specimen and the light transmissive substrate relative to each other;
   illumination means for illuminating the light transmissive substrate with white light from the opposite side of light transmissive substrate to the specimen;
   interference image acquisition means for acquiring an interference image produced by the light reflected off the specimen and the light reflected off the light transmissive substrate;

intensity histogram creation means for creating an intensity histogram from information on the intensity of the interference image; and image analysis and computation means for calculating an intensity difference histogram from the intensity histogram.

10. The contact area measuring apparatus according to claim 9, wherein the intensity histogram creation means forms separate RGB intensity information from the information on the intensity of the interference image and creates a G-intensity histogram.

11. The contact area measuring apparatus according to claim 9, wherein the image analysis and computation means calculates an intensity difference histogram from the intensity histogram and determines the region of the intensity difference histogram that has positive values.

12. A contact area measuring apparatus comprising:
a light transmissive substrate in contact with a specimen;
driving means for moving the specimen and the light transmissive substrate relative to each other;
illumination means for illuminating the light transmissive substrate with white light from the opposite side of the light transmissive substrate to the specimen;
interference image acquisition means for acquiring an interference image produced by the light reflected off the specimen and the light reflected off the light transmissive substrate; and
image analysis and computation means for using information on the intensity of the interference image as a tracking marker.

13. The contact area measuring apparatus according to claim 12, wherein the interference image acquisition means acquires an interference image and information on the intensity of the interference image.

14. The contact area measuring apparatus according to claim 12, wherein the image analysis and computation means calculates a velocity vector by using the information on the intensity of the interference image as a tracking marker.

15. A contact area measuring method comprising the steps of:
placing a specimen on a light transmissive substrate so that the specimen comes into contact with the light transmissive substrate;
moving the specimen and the light transmissive substrate relative to each other;
illuminating the light transmissive substrate with white light from the opposite side of the light transmissive substrate to the specimen;
acquiring an interference image produced by the light reflected off the specimen and the light reflected off the light transmissive substrate;
creating an intensity histogram from information on the intensity of the interference image; and
calculating an intensity difference histogram from the intensity histogram.

16. The contact area measuring method according to claim 15, wherein separate RGB intensity information is formed from the information on the intensity of the interference image and a G-intensity histogram is created in the intensity histogram creation step.

17. The contact area measuring method according to claim 15, wherein:
an intensity difference histogram is calculated from the intensity histogram; and
the region of the intensity difference histogram that has positive values is determined.

18. A contact area measuring method comprising the steps of:
placing a specimen on a light transmissive substrate so that the specimen comes into contact with the light transmissive substrate;
moving the specimen and the light transmissive substrate relative to each other;
illuminating the light transmissive substrate with white light from the opposite side of the light transmissive substrate to the specimen;
acquiring an interference image produced by the light reflected off the specimen and the light reflected off the light transmissive substrate; and
using information on the intensity of the interference image as a tracking marker.

19. The contact area measuring method according to claim 18, wherein an interference image and information on the intensity of the interference image are acquired in the interference image acquisition step.

20. The contact area measuring method according to claim 18, wherein a velocity vector is calculated by using the information on the intensity of the interference image as a tracking marker.

* * * * *